(12) United States Patent
Schoenbach et al.

(10) Patent No.: US 10,660,693 B2
(45) Date of Patent: May 26, 2020

(54) ELECTROMANIPULATION OF CELLS AND OTHER BIOLOGICAL TISSUES BY PULSED ELECTRIC FIELDS AT ELEVATED TEMPERATURES

(71) Applicant: OLD DOMINION UNIVERSITY RESEARCH FOUNDATION, Norfolk, VA (US)

(72) Inventors: Karl H. Schoenbach, Norfolk, VA (US); Richard Heller, Norfolk, VA (US); James Camp, King George, VA (US); Stephen P. Beebe, Norfolk, VA (US); Shu Xiao, Norfolk, VA (US); Amy Donate, Yorktown, VA (US)

(73) Assignee: Old Dominion University Research Foundation, Norfolk, VA (US)

( * ) Notice: Subject to any disclaimer, the term of this patent is extended or adjusted under 35 U.S.C. 154(b) by 119 days.

(21) Appl. No.: 16/057,115

(22) Filed: Aug. 7, 2018

(65) Prior Publication Data
US 2019/0038337 A1    Feb. 7, 2019

Related U.S. Application Data

(63) Continuation of application No. 14/366,909, filed as application No. PCT/US2012/070874 on Dec. 20, 2012, now Pat. No. 10,070,914.
(Continued)

(51) Int. Cl.
*A61B 18/12* (2006.01)
*A61N 1/40* (2006.01)
(Continued)

(52) U.S. Cl.
CPC .......... *A61B 18/1206* (2013.01); *A61B 18/12* (2013.01); *A61N 1/327* (2013.01);
(Continued)

(58) Field of Classification Search
CPC ..... A61B 18/12; A61B 18/1206; A61B 18/18; A61B 18/1815; A61B 18/20; A61B 18/24;
(Continued)

(56) References Cited

U.S. PATENT DOCUMENTS 5,536,267 A    7/1996    Edwards et al.
7,496,401 B2   2/2009    Bernabei
(Continued)

OTHER PUBLICATIONS

Altunc, S, Baum, C.E., Christodoulou, C.G., Schamiloglu, E. and Buchenauer, C. J., "Focal waveforms for various source waveforms driving a prolate-spheroidal impulse radiating antenna (IRA)," Radio Sci. 43: RS4S13 (2008).
(Continued)

*Primary Examiner* — Kami A Bosworth
*Assistant Examiner* — Leah J Swanson
(74) *Attorney, Agent, or Firm* — Fish & Richardson P.C.

(57) ABSTRACT

Systems and methods for treatment of a biological tissues including target tissues and other tissues. The method includes elevating a temperature of the target tissues above a physiological temperature of the biological tissues to treatment temperature, and generating an electric field extending through at least a portion of the target tissues using a pre-defined sequence of short voltage pulses applied between at least two electrodes. In the method, the treatment temperature is maintained during the generating. Further, the pre-defined sequence is selected such that a magnitude of the electric field generated is sufficient to induce electromanipulation in the portion of the target tissues without substantially elevating of the temperature of the portion of the target tissues above the treatment temperature.

24 Claims, 19 Drawing Sheets

Related U.S. Application Data

(60) Provisional application No. 61/578,141, filed on Dec. 20, 2011.

(51) Int. Cl.

| | |
|---|---|
| A61N 1/32 | (2006.01) |
| A61N 5/00 | (2006.01) |
| A61N 5/02 | (2006.01) |
| A61N 5/06 | (2006.01) |
| A61B 18/18 | (2006.01) |
| A61B 18/20 | (2006.01) |
| A61B 18/00 | (2006.01) |
| A61N 5/067 | (2006.01) |
| A61B 18/24 | (2006.01) |

(52) U.S. Cl.
CPC .............. *A61N 1/403* (2013.01); *A61N 5/00* (2013.01); *A61N 5/025* (2013.01); *A61N 5/0625* (2013.01); *A61B 18/1815* (2013.01); *A61B 18/20* (2013.01); *A61B 18/24* (2013.01); *A61B 2018/00613* (2013.01); *A61B 2018/00761* (2013.01); *A61B 2018/00767* (2013.01); *A61B 2018/00791* (2013.01); *A61B 2018/00994* (2013.01); *A61N 2005/067* (2013.01); *A61N 2005/0651* (2013.01); *A61N 2005/0666* (2013.01)

(58) Field of Classification Search
CPC .. A61B 2018/1807; A61B 2018/00613; A61B 2018/00791; A61B 2018/00994; A61N 1/403; A61N 1/327; A61N 5/025; A61N 5/0625

See application file for complete search history.

(56) References Cited

U.S. PATENT DOCUMENTS

| 10,070,914 B2 | 9/2018 | Schoenbach et al. |
| 2003/0204161 A1 | 10/2003 | Ferek-Petric |
| 2005/0004507 A1 | 1/2005 | Schroeppe et al. |
| 2006/0217703 A1 | 9/2006 | Chornenky et al. |
| 2009/0125091 A1 | 5/2009 | Schoenbach et al. |
| 2012/0035511 A1 | 2/2012 | Schoenbach et al. |

OTHER PUBLICATIONS

Bates D. A., C. L. Grimellec, and J. H. T. Bates, "Effects of Thermal Adaptation at 40.degree. C. on Membrane Viscosity and the Sodium-Potassium Pump in Chinese Hamster Ovary Cells," Cancer Research, pp. 4895-4899, 1985.
Baum C. E., "Focal Waveform of a Prolate-Spheroidal IRA", SSN Note, 509, Feb. 2006.
Beebe et al., Nanosecond, high-intensity pulsed electric fields induce apoptosis in human cells FASEB J., 2003, 17:1493-1495.
Berendsen H. J. C., D. van der Spoel D, R. van Drumen, "Gromacs: a message-passing parallel molecular dynamics implementation," Comput. Phys. Commun. vol. 91, pp. 43-56, 1995.
Blicher A., K. Wodzinska, M. Fidorra, M. Wnter Halter, and T. Heimburg, "The temperature dependence of lipid membrane permeability, its quantized nature, and the influence of anesthetics," Biophys. J., vol. 96, pp. 4581-4591, Jun. 2009.
Camp J. Thomas, "The Synergistic Effect of Temperature and Subnanosecond Pulsed Electric Fields on Biological Cells," Dissertation, Old Dominion University, May 2012.
Cetas et al., "Status and future developments in the physical aspects of hyperthermia," Cancer Research, 44, pp. 4894-4901, 1984.
Chen X., J. F. Kolb, R. J. Swanson, K H. Schoenbach and S. J. Beebe, "Apoptosis initiation and angiogenesis inhibition: Melanoma targets for nanosecond pulsed electric fields," Pigment Cell and Melanoma Research, vol. 23, pp. 554-563,1 2010.
Dickson et al., "Temperature Range and Selective Sensitivity of Tumors to Hyperthermia: A Critical Review," Annals New York Academy of Sciences, vol. 335, pp. 180-205, 1980.
Frey W., J. A. White, R. O. Price, P. F. Blackmore, R. P. Joshi, R. Nuccitelli, S. J. Beebe, K. H. Schoenbach, and J. F. Kolb, "Plasma Membrane Voltage Changes During Nanosecond Pulsed Electric Field Exposure," Biophys. J. vol. 90, pp. 3608-3615, 2006.
Garner A., G. Chen, N. Chen, V. Sridhara, J. Kolb, R. Swanson, S. Beebe, R. Joshi, and K. Schoenbach, "Ultrashort electric pulse induced changes in cellular dielectric properties", Biochem. Biophys. Res. Comm., vol. 362, pp. 139-144, 2007.
Garon, E.B. et al., In vitro and in vivo evaluation and a case report of intense nanosecond pulsed electric field as a local therapy for human malignancies, Int J Cancer, 2007, 675-82, 121, Wiley-Liss, Inc.
Gehl J., "Electroporation: Theory, and methods, perspectives for drug delivery, gene therapy and research," Acta. Physiol. Scand., vol. 177, pp. 437-447, 2003.
Green D. R., "Apoptotic Pathways: Ten Minutes to Dead," Cell, vol. 121, No. 5, pp. 671-674, 2005.
Heeren T., J. T. Camp, J. F. Kolb, K. H. Schoenbach, S. Katsuki, and H. Akiyama, "250 kV Subnanosecond Pulse Generator with Adjustable Pulsewidth," IEEE Trans. Diel. Electr. InsuL, vol. 14, pp. 884-888, 2007.
"Heller et at., ""In vivo electroporation for gene therapy"" Human GeneTherapy,2006; 17:890-897".
Hildebrandt et al., "The cellular and molecular basis of hyperthermia," Oncology Hematology, 43, pp. 33-56, 2002.
Hu Q., R. P. Joshi, and K. H. Schoenbach, "Simulations of nanopore formation and phosphatidylserine externalization in lipid membranes subjected to a high-intensity, ultrashort electric pulse," Phys. Rev., vol. 72, pp. 1539-3755, 2005.
Hu Q., V. Sridhara, R. P. Joshi, J. F. Kolb, and K. H. Schoenbach, "Molecular Dynamics Analysis of High Electric Pulse Effects on Bilayer Membranes Containing DPPC and DPPS," IEEE Trans. Plasma Science., vol. 34, No. 4, pp. 1405-1411, 2006.
Jayaram et al., "Effects of High Electric Field Pulses on Lactobacillus Brevis at Elevated Temperatures," Conference Record of the 1991 IEEE Industry Applications Society Annual Meeting, vol. 1, pp. 674-681, Oct. 1991.
Joshi R. P., Q. Hu, R. Aly, K. H. Schoenbach, and H. P. Hjalmarson, "Self-Consistent Simulations of Electroporation Dynamics in Biological Cells Sujected to Ultrashort Electrical Pulses," Phys. Rev. E, vol. 64, 011913 pp. 1-10, 2001.
Kolb J. F., S. Xiao, J. T. Camp, M. Migliaccio, C. Bajracharya, and K. H. Schoenbach, "Sub-nanosecond electrical pulses for medical therapies and imaging," 2010 Proceedings of the Fourth European Conference on Antennas and Propagation (EuCAP), pp. 1-5, Apr. 12-16, 2010.
Kroemer G., L. Galluzzi, P. Vandenabeele, J. Abrams, E. S. Alnemn, E. H. Baehrecke, M. V. Blagosklonny, W. S. El-Deiry, P. Golstein, D. R. Green, M. Hengartner, R. A. Knight, S. Kumar, S. A. Lipton, W. Malomi, G. Nunez, M. E. Peter, J. Tschopp, J. Yuan, M. Piacentini, B. Zhivotovsky, G. Melino; Nomenclature Committee on Cell Death 2009. Classification of cell death: Recommendations of the Nomenclature Committee on Cell Death 2009. Cell Death Differ. vol. 16, No. 1, pp. 3-11, 2009.
Lindahl E., B. Hess, D. van der Spoel, "A package for molecular simulation and trajectory analysis," J. Mol. Model. vol. 7, pp. 306-317, 2001.
Martiniere A., M. Shedunova, A. J. W. Thomson, N. H. Evans, S. Penfieldd, J. Runions, and H. G. McWatters, "Homeostasis of Plasma Membrane Viscosity in Fluctuating Temperatures," New Phytologist, vol. 192, pp. 328-2337, 2011.
Mir et al., "Introduction of definite amounts of nonpermeant molecules into living cells after electropermeabilization: direct access to the cytosol" Exp Cell Res 1988; 175: 15-25.
Nuccitelli et al., A new pulsed electric field therapy for melanoma disrupts the tumor's blood supply and causes complete remission without recurrence Int J Cancer, 2009, 125:438-445.
Nuccitelli et al., "Nanosecond pulsed electric fields cause melanomas to self-destruct," Biochem. Biophys. Res. Commun., vol. 343, No. 2, pp. 351-360, 2006.

(56) References Cited

OTHER PUBLICATIONS

Oshima et al., ""Effect of culture temperature on high voltage pulse sterilization of *Escherichia coli*,"" Journal of Electrostatics, vol. 55, pp. 227-235, 2002.

Ren W., S. J. Beebe, "An apoptosis targeted stimulus with nanosecond pulsed electric fields (nsPEFs) in E4 squamous cell carcinoma," Apoptosis, vol. 16, pp. 382-393, 2011.

Schmidt C. R., P. Shires and M. Mootoo, "Real-time ultrasound imaging of irreversible electroporation in a porcine liver model adequately characterizes the zone of cellular necrosis," HPB (Oxford), vol. 14, pp. 98-102, 2012.

Schoenbach K. H., R. P. Joshi, S. Beebe, and C. Baum, "A scaling law for membrane permeabilization with nanopulses," IEEE Trans Diet. Elect. Insul., vol. 16, No. 5, pp. 1224-1235, 2009.

Schoenbach K. H., S. Xiao, R. P. Joshi, J. T. Camp, T. Heeren, J. F. Kolb, S. J. Beebe, "The Effect of Intense Subnanosecond Electrical Pulses on Biological Cells," IEEE Trans. Plasma Science, vol. 36, No. 2, pp. 414-422, 2008.

Schoenbach, K.S. et al. Bioelectric Effects of Intense Nanosecond Pulses. IEEE Transactions on Dielectrics and Electrical Insulation 14, 1088-1109 (2007).

Sevgi L. and C. Uluisik, "Transmission Line Fault Analysis Using a Matlab Based Virtual Time Domain Reflectometer Tool," IEEE Ant. and Prop. Mag., pp. 141-145, 2006.

Song et al., ""Synergistic effects of local temperatureenhancements on cellular responses in the context of high-intensity, ultrashort electric pulses,"" Med. Biol. Eng. Comput., vol. 49, pp. 713-718, 2011.

Thomson K. R., W. Cheung, S. J. Ellis, D. Federman, H. Kavnoudias, D. Loader-Oliver, S. Roberts, P. Evans, C. Ball, and A. Haydon, "Investigation of the safety of irreversible electroporation in humans," J Vasc. Interv. Radiol. vol. 22, pp. 611-621, 2011.

Tsong, Electroporation of cell membranes., Biophysical journal, 1991, 60(2):297-306.

Weaver J. C., "Electroporation of Cells and Tissue," IEEE Trans. Plasma Sci, vol. 28, No. 1, pp. 24-33, 2000.

Xiao S., K. H. Schoenbach, and C. E. Baum, "Time-Domain Focusing Radar for Medical Imaging," Proc. URSI, XXIX Sen. Assembly of URSI, Chicago, Ill., 2008, http://ursi-franceinstitut-telecom.fr/pages/pages_ursi/URSIGA08/papers/E-02p4.pdf.

Xiao S., S. Guo, V. V. Nesin, R. Heller, and K. H. Schoenbach, "Subnanosecond electric pulses cause membrane permeabilization and cell death," IEEE Trans. Biomed. Eng., vol. 58, No. 5, pp. 1239-1245, 2011.

Huang J., W. Ren, Y. Jing, J. F. Kolb, "Dielectric Evolution of Mammalian Cell Membranes after Exposure to Pulsed Electric Fields," IEEE Trans. Dielectr. Electr. Insul., vol. 19, No. 2, pp. 609-622, 2012.

Cetas et al., "Status and future developments in the physical aspects of hyperthermia", Cancer Research (1984) 44: 4894-4901.

Dickson et al., "Temperature range and selective sensitivity of tumors to hypothermia: A critical review", Annals New York Academy of Sciences (1980) 335: 180-205.

Heller et al., "In vivo electroporation for gene therapy", Human Gene Therapy (2006) 17: 890-897.

Hildebrandt et al., "The cellular and molecular basis of hypothermia", Critical Reviews in Oncology Hematology (2002) 43: 33-56.

Jayaram et al., "Effects of high electric field pulses on Lactobacillus Brevis at elevated temperatures", Industry Applications Society Annual Meeting (1991) 1: 674-681.

Mir et al., "Introduction of definite amounts of nonpermeant molecules into living cells after electropermeabilization: Direct access to cytosol", Exp Cell Res (1988) 175: 15.

Nuccitelli et al., "Nanosecond pulsed electric fields cause melanomas to self-destruct", Biochem Biophys Res Commun (May 2006) 343(2): 351-360.

Ohshima et al., "Effect of culture temperature on high voltage pulse sterilization of *Escherichia coli*", Journal of Electrostatics (2002) 55: 227-235.

Song et al., "Synergistic effects of local temperature enhancements on cellular responses in the context of high-intensity, ultrashort electric pulses", Med Biol Eng Comput.

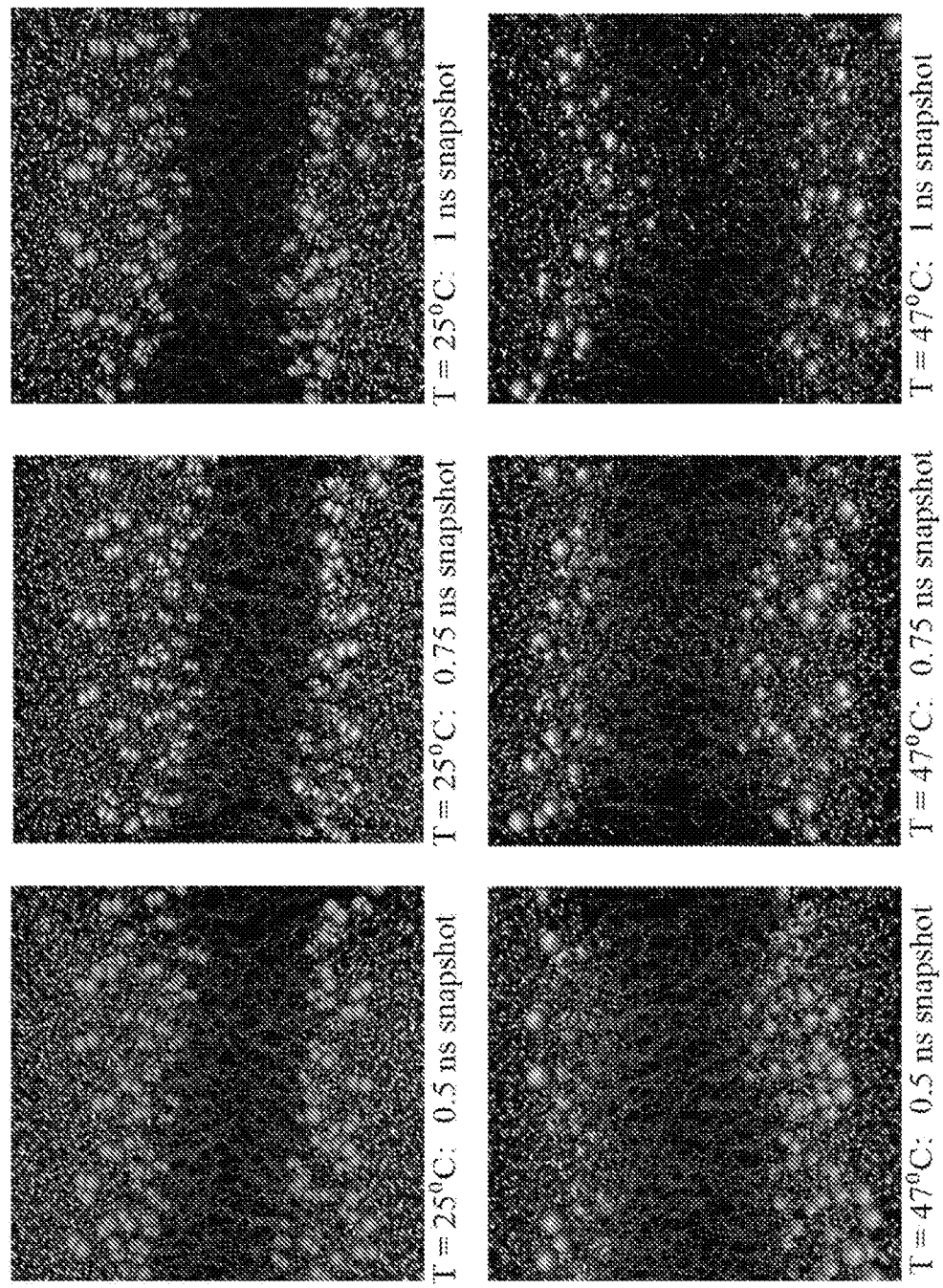

ELECTROMANIPULATION OF CELLS AND OTHER BIOLOGICAL TISSUES BY PULSED ELECTRIC FIELDS AT ELEVATED TEMPERATURES

CROSS-REFERENCE TO RELATED APPLICATION

This application is a continuation of and claims the priority to U.S. Non-Provisional Application No. 14/366,909 entitled "ELECTROMANIPULATION OF CELLS AND OTHER BIOLOGICAL TISSUES BY PULSED ELECTRIC FIELDS AT ELEVATED TEMPERATURES", filed Jun. 19, 2014, now U.S. Patent No. 10,070,914, issued Sep. 11, 2018, which is a U.S. National Phase Application of International Application No. PCT/US2012/070874, entitled "ELECTROMANIPULATION OF CELLS AND OTHER BIOLOGICAL TISSUES BY PULSED ELECTRIC FIELDS AT ELEVATED TEMPERATURES", filed Dec. 20, 2012, which claims priority to U.S. Provisional Patent Application No. 61/578,141, entitled "INCREASE OF CELL LETHALITY CAUSED BY ELECTRICAL PULSES THROUGH HEATING OF TISSUE" and filed Dec. 20, 2011.

FIELD OF THE INVENTION

The present invention relates to, and more specifically to apparatus and methods for electromanipulation of cells and other biological tissues. More specifically, the invention relates to apparatus and methods for delivering non-ionizing radiation to the tissue, to provide thermal energy, and subsequently or simultaneously providing electrical pulses for electromanipulation to induce electroporation or to stimulate death in cells and other biological tissues, where the combination of the two effects results in enhanced uptake of pharmacological or biological agents or enhanced ablation of cells and biological tissues.

BACKGROUND

Hyperthermia as a method to treat cancer, either by just its thermal effects or in combination with other agents (e.g., radiative cancer treatments) and has been explored for over 30 years See Hildebrandt, B, Wust, P., Ahlers, O., Dieing, A., Sreenivasa, G., Kerner, T., Felix, R., and Riess, H., 2002, "The cellular and molecular basis of hyperthermia," Critical Reviews in Oncology Hematology, 43, pp. 33-56; Cetas, T. C and Roemer, R. B, 1984, "Status and future developments in the physical aspects of hyperthermia," Cancer Research, 44, pp. 4894-4901). In such treatment methods, the temperature range generally does not exceed 42° C., but studies up to almost 50° C. have been performed. See, e.g., Dickson, J. A. and Calderwood, S. K., 1980, "Temperature Range and Selective Sensitivity of Tumors to Hyperthermia: A Critical Review," Annals New York Academy of Sciences, Vol. 335, pp. 180-205. Further, it is known that by increasing the temperature it is possible to reduce the exposure time. For example, Dickson and Calderwood (1980) have reported that hyperthermia can be obtained by increasing the local body temperature to about 50° C. Under such conditions, an exposure time on the order of 0.1 hours (6 minutes) was required to provide an effective treatment.

It is also known, that short pulses from milliseconds to nanoseconds can be used to initiate cell death. For example, melanoma tumors in mice have been successfully treated with 300 ns pulsed electrics fields with electric field strengths up to 60 kV/cm. See R. Nuccitelli, U. Pliquett, X. Chen, W. Ford, J. Swanson, S. J. Beebe, J. F. Kolb, and K. H. Schoenbach, "Nanosecond pulsed electric fields cause melanomas to self-destruct," Biochem. Biophys. Res. Commun., vol. 343, no. 2, pp. 351-360, 2006). These pulses were delivered to the tumor with needle electrodes, or with plate electrodes surrounding the tumor. In contrast to hyperthermia treatments, such pulse treatments are based on non-thermal effects.

Studies combining these two effects, and controlling them independently of each other, has been limited to the studies of bacteria. See S. Jayaram, G. S. P. Castle, and A. Margaritis, "Effects of High Electric Field Pulses on Lactobacillus Brevis at Elevated Temperatures," Conference Record of the 1991 IEEE Industry Applications Society Annual Meeting, vol. 1, pp. 674-681, October 1991, T. Ohshima, K. Okuyama, M. Sato, "Effect of culture temperature on high voltage pulse sterilization of Escherichia coli," Journal of Electrostatics, vol. 55, pp. 227-235, 2002. In such studies, the pulse durations were on the order of microseconds. Further, these studies indicated some enhancement at 60° C. compared to 30° C. In particular, the initial live cell count was $10^9$ cells/cm$^3$ at 30° C. The live cell count then decreased to $10^7$ cells/cm$^3$ when the temperature was increased to 60° C. for ten seconds. When exposed to 60 pulses (on the order of microseconds) of an amplitude of about 30 kV/cm, the live cell count decreased to $10^4$ cells/cm at 30° C. and the live cell count was negligible at 60° C.

The cause of cell death of bacteria due to the applied electric fields was assumed to be due to electroporation. The increase in temperature causes an increase in the conductivity of the medium and cytoplasm of the cell, as well as a decrease in the viscosity of the membrane. Based on the increase in membrane and cytoplasm conductivity, it was concluded that the observed increase in cell death at higher temperature is due to a more rapid increase in membrane potential, leading to an earlier breakdown of the membrane. Similar results were obtained with E. coli in which an increase in bacteria death was observed when pulses at elevated temperatures were applied. Here, it was also assumed that this effect is due to a decrease in membrane viscosity.

It is known that cells exposed to certain pulsed electric fields will have increased permeability and enable nonpermeant molecules to enter the cell. This has been demonstrated for a variety of molecules including chemotherapeutic agents (Mir L M, Banoun H, Paoletti C. Introduction of definite amounts of nonpermeant molecules into living cells after electropermeabilization: direct access to the cytosol. Exp Cell Res 1988; 175:15-25) and nucleic acids (Heller, L and Heller R, In vivo electroporation for gene therapy, Human Gene Therapy, 2006; 17:890-897) among other molecules. Pulsed electric fields can also manipulate molecules to enable cell fusion as well as insertion of molecules into cell membranes. Combination of heat and electric pulses will facilitate these interactions due to the decrease in viscosity and increased fluidity of the cell membrane.

SUMMARY

In a first embodiment of the invention, a method for treatment of biological tissues including target tissues and other tissues is provided. The method includes elevating a temperature of the unwanted tissues above a physiological temperature of the biological tissues to treatment temperature, and generating an electric field extending through at least a portion of the target tissues using a pre-defined sequence of short voltage pulses applied between at least two electrodes. In the method, the treatment temperature is maintained during the generating, and the pre-defined sequence is selected such that a magnitude of the electric field generated is sufficient to induce electromanipulation in the portion of the target tissues without substantially elevating of the temperature of the portion of the target tissues above the treatment temperature.

In the method, the treatment temperature can be selected to be less than 20° C. higher than the physiological temperature. Further, the generating can include selecting the duration of the short voltage pulses to be between about 50 ps and about 800 ms. Additionally, the generating can also include selecting the sequence of short voltage pulses so that the magnitude of the electric field is between about 20 V/cm and about 1000 kV/cm, such as greater than about 70 kV/cm.

In the method, the elevating can include exposing the biological tissue to non-ionizing radiation. The exposing can include selecting the source of the non-ionizing radiation to be one of a lamp, a laser, a photodiode, a microwave source, or a millimeter wave source operating with a wavelength in the range between about 0.4 micrometers and about 10 cm. Further, the non-ionizing radiation can be directed to the biological tissues via at least one of a lens, a mirror or reflector, an optical fiber, or a waveguide coupled to a source of the non-ionizing radiation. In the method, the one of the lens, the mirror or reflector, the optical fiber, or the waveguide can be configured so that the non-ionizing radiation is directed primarily at the unwanted tissues.

In the method, the optical fiber or waveguide can be disposed in one of a needle or catheter, and wherein the elevating can further include inserting the one of the needle or catheter into the biological tissue, and activating the source of non-ionizing radiation.

The method can further include introducing at least one of a pharmacological agent or a biological agent to the biological tissues during the directing.

In a second embodiment of the invention, a system for treatment of biological tissues comprising target tissues and other tissues is provided. The system includes a radiation source configured for generating non-ionizing radiation, a pulse generator configured for generating a plurality of voltage pulses, a plurality of electrodes, coupled to the pulse generator and arranged so that an electric field resulting from the plurality of pulses and between the plurality of electrodes traverses at least a portion of the target tissues, at least one guide device for directing the non-ionizing radiation and the electromagnetic energy to at least the portion of the target tissues, a temperature probe for measuring a temperature of at least the portion of the target tissues, and a processor coupled to the radiation source, the pulse generator, and the temperature probe.

The processor is configured for causing the radiation source to generate the non-ionizing radiation in an amount sufficient to elevate a temperature of the biological tissue above a physiological temperature of the biological tissue to a treatment temperature, and causing the pulse generator to generate a pre-defined sequence of short voltage pulses. In the system, the treatment temperature is maintained during the generating, and the pre-defined sequence is configured to cause a magnitude of the electric field to be sufficient to induce electromanipulation in the portion of the target tissues without substantially elevating of the temperature of the portion of the target tissues above the treatment temperature.

In the system, the processor can be further configured for controlling the radiation source to elevate the temperature by less than 20° C. Further, the processor can be configured for causing the pulse generator to provide a duration of the short voltage pulses to be between about 50 ps and about 800 ms. Additionally, the processor can be further configured to cause the pre-defined sequence of short voltage pulses to be generated so that the electric field is generated that is between 20 V/cm and 1000 kV/cm, such as greater than 70 kV/cm.

In the system, the non-ionizing radiation source can be a lamp, a laser, a microwave or a millimeter wave source operating with a wavelength in the range between about 0.4 micrometers and 10 cm. Further, the at least one guide device can be one of a lens, a mirror, an optical fiber or a waveguide. Additionally, the optical fiber or waveguide can be disposed in one of a needle or catheter insertable into the biological tissue.

In the system, the system of claim 12, wherein the plurality of electrodes can be needle-type or plate-type electrodes.

BRIEF DESCRIPTION OF THE DRAWINGS

FIG. 16 shows molecular dynamic simulations of a lipid bilayer exposed to a constant electric field strength of 0.5 V/nm for 1 ns at 25° C. and 47° C.

DETAILED DESCRIPTION

Figure 1A:
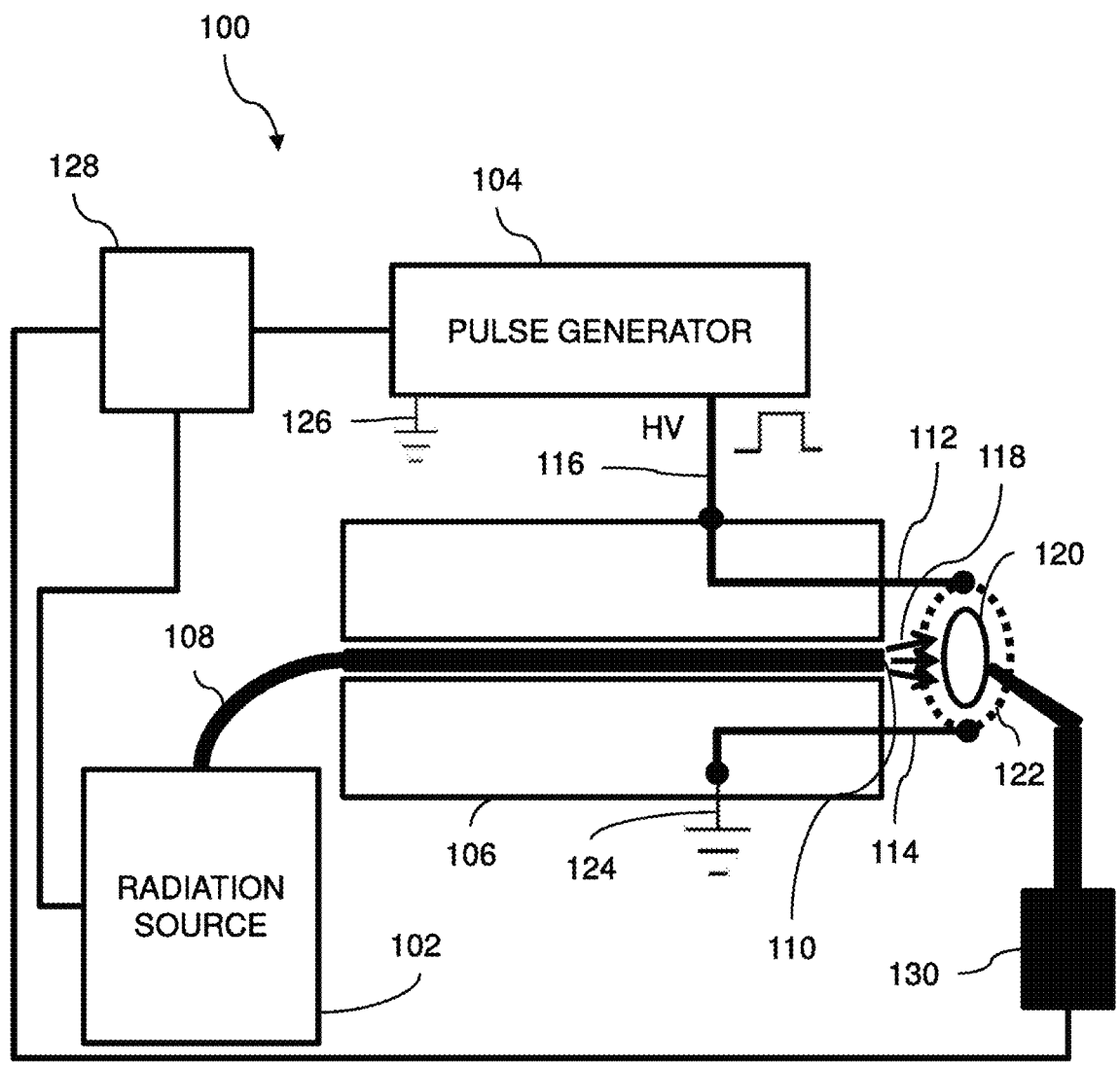
FIG. 1A is a schematic illustration of a system in accordance with the various embodiments.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

The various embodiments are directed to systems and methods for treatment of cells and other biological tissues in subjects, including human and non-human subjects. More specifically, the invention relates to apparatus and methods for delivering non-ionizing radiation to the tissue, to provide thermal energy, and subsequently or simultaneously providing electrical pulses for electromanipulation of cells and other biological tissues and/or to stimulate cell death or death of other biological tissues, where the combination of the two effects provides enhanced electroporation and/or tissue ablation.

The tissue to be treated can be tumor tissue, or adipose tissue, or and other tissues which are desired to be treated or removed. In the case of inducing electroporation, the various embodiments contemplate that such electroporation can be accompanied by delivery of pharmacological agents or biological agents (e.g., genes, viruses, proteins, etc., . . . ) to tissues to stimulate a therapeutic response other than ablation or to further enhance ablation. Further such tissues can be adjacent to healthy tissues, which preferably are not to be treated or ablated.

Although some embodiments will be described with respect to cell death or tissue ablation, such embodiments are not limited in that regard. Rather, such embodiments can also be adapted to provide electromanipulation for purposes of stimulating a therapeutic response in the targeted cells and biological tissues.

Methods according to the various embodiments include providing a radiation source or other device for generating non-ionizing radiation, means to transfer this radiation to a target tissue, a pulse generator other device for generating a plurality of voltage pulses, and means for using these voltage pulses to apply pulsed electric fields to the target tissue. One such exemplary system illustrated in FIG. 1A.

FIG. 1A is a schematic illustration of a system 100 in accordance with the various embodiments. As shown in FIG. 1A, system 100 includes, a radiation source 102, a pulse generator 104, a holder 106, a radiation waveguide 108, an emitter 110, electrodes 112 and 114, and an electrical waveguide 116.

As shown in FIG. 1A, the holder 106 is utilized to combine the electrodes 112 and 114, the waveguide 108, and the emitter 110 into a single unit via. In such a configuration, the holder 106 can be constructed from electrically insulating materials to electrically isolate the electrodes 112 and 114 from each other. Additionally, in the case where there waveguide 108 and emitter consist of electrical components, such a holder can also be used to electrically isolate the various components.

The radiation source 102 can be any device capable of generating non-ionizing electromagnetic radiation. For example, this can include sources for generating near ultraviolet radiation, visible light, infrared radiation, microwave radiation, radio waves (e.g., TV, AM, FM), and low-frequency radiofrequency waves (e.g., longwave radiation). That is, any type of radiation that does not carry enough energy to cause significant ionization of the atoms or molecules in a target tissue, but rather just enough radiation to excite electrons in such atoms or molecules into higher energy states so as to increase the temperature of the target tissues. For example, the radiation source 102 can be configured for providing a wavelength of the non-ionizing radiation to be between 0.4 micrometers and 10 cm. This covers the visible spectral range, the IR spectral range, the Terahertz spectral range, the millimeter wave spectral range and part of the microwave spectral range.

Although the various embodiments will be described primarily with respect to radiation source using light sources, the various embodiments are not limited in this regard. Further, one of ordinary skill in the art will recognize that any components shown herein and applicable to light sources can be replaced with suitable analogous components for other types of radiation sources.

Further, power, power density, and specific electrical energy can be selected in the various embodiments. In some embodiments, the power levels of the radiation can vary from about 1 mW to 1 kW. The power density levels can vary from about 1 mW/cm$^2$ to 1 kW/cm$^2$. The specific electrical energy levels can be varied from about 1 J/cm$^3$ to 500 J/cm$^3$.

The radiation source 102 can be coupled, via a radiation waveguide 108, to the emitter 110 in holder 106. The emitter 110 can be figured so as to direct the non-ionizing radiation 118 towards target tissues 120. As noted above, the target tissues are disposed in or are adjacent to other tissue, such as healthy tissues. These other tissues are not illustrated in the various drawings for ease of illustration. However, one of ordinary skill in the art will readily recognize that the electrodes 112, 114 would be positioned such that biological tissues, including both the unwanted target tissues and other tissues, may be disposed between the electrodes such that a generated electric field is directed through at least the unwanted target tissues.

The radiation waveguide 108 and the emitter 110 can be selected in accordance with the type of radiation generated by radiation source 102. For example, in the case of visible light being generated by radiation source 102, the radiation waveguide 108 can be an optical fiber and the emitter 110 can be defined by an end of the radiation waveguide 108. In the case of radio waves, the waveguide 108 and the emitter 110 can be an electrical conductor and an antenna, respectively, where the electrical conductor carries the radio wave signals to the antenna that radiates them toward target tissues 120. Similarly, the radiation waveguide 108 and the emitter 110 can be selected to be components appropriate for the radiation type.

The pulse generator 104 can be any device or combination of devices for generating a plurality of high voltage pulses. The pulse generator 104 is configured to generate a plurality of voltage pulses with a voltage in the range of about 100V and about 300 kV. Further, the pulse generator 104 is configured to provide such pulses such that the pulse duration of these pulses is in the range between 50 ps to 800 ms. Additionally, the pulse generator 104 is configured to provide a pulse repetition rate to be between about 1 Hz and about 10000 Hz. The electric field generated under such conditions can be between about 20 V/cm and about 1000 kV/cm, such as greater than 70 kV/cm In general, the multiplicity in parameters (electric field intensity, pulse duration, pulse number, pulse shape, pulse sequence, target cells, target tissue, temperature increase, duration of temperature pulse) which determine the electroporation threshold make it is difficult to determine a range for which to expect the thermally assisted electroporation. However, the more dominant parameters tend to be pulse duration and electric field intensity. Accordingly, some exemplary ranges for these parameters, for purposes of inducing electroporation, are: 50 ps to 1 microsecond pulse durations with magnitudes for $10^6$ V/cm to 1 kV/cm for the electric field and 1 microsecond to 800 ms with magnitudes of 10 kV/cm to 20 V/cm for the electric field. However, the various embodiments are not limited to these specific ranges.

In system 100, the pulse generator 104 is configured to generate the plurality of voltage pulses between the electrodes 112, 114, extending from holder 106 so that an electric field 122 through the target tissues is generated. As shown in FIG. 1A, the electrodes 112, 114 are configured so that a first electrode 112 is coupled to the pulse generator 104 via electrical waveguide 116 and the second electrode 114 is coupled to a ground or other reference node.

Although FIG. 1A illustrates separate ground nodes for pulse generator 104 and holder 106, nodes 126 and 124 respectively, the various embodiments are not limited in this regard. Rather these nodes can be coupled together. Further, in some embodiments, the reference nodes 124 and 126 can be controlled separately and need not be at the same reference voltage.

In the various embodiments a control unit 128 can be provided. The control unit 128 can be configured to control and synchronize the operation of radiation source 102 and pulse generator 104 so that the timing of the irradiating versus pulsing is controlled. This unit 128 is controlled again by signals from temperature probes 130 which record the temporal development of the tissue temperature. As shown in FIG. 1A, the temperature probe 130 can be a probe which measures the temperature at the irradiated tissue through physical contact, such as a thermocouple. However, the various embodiments are not limited in this regard. In other embodiments, the temperature probe can be configured as an optical probe which measures the temperature based on the radiation emitted from the heated tissue surface. In such configurations, this second kind of probe can be incorporated through a fiber in holder 106. For example, the optical probe could be coupled to a fiber in holder 106 running parallel to the waveguide 108.

The various embodiments also contemplate that separate control units (not shown) can be provided for each of the radiation source 102 and the pulse generator 104. Thus, a first control unit can control both the intensity of the radiation as well as the duration of the irradiation. A second control unit can then control the pulse duration amplitude, number and repetition rate. In such a configuration, the two units will still need to be synchronized by means of a third unit which controls the timing of irradiation versus pulsing.

The delivery systems for the non-ionizing radiation and the electrical pulses can be separate systems, or can be combined in a single device, which allows to deliver both the radiation as well as the electrical pulses through a single delivery device. For example, in the case of separate systems, the source of the non-ionizing radiation can be the same as described in FIG. 1A or can be one of a lamp, a laser, a microwave source, or a millimeter wave source operating with a wavelength in the range between about 0.4 micrometers and about 10 cm.

System 100 operates as follows. First, the radiation source 102 is configured to generate the non-ionizing radiation and it is directed, via radiation waveguide 108, to emitter 110. Emitter 110 then emits the non-ionizing radiation 118 to the target tissues 120 in order to raise the temperature of the target tissues up to about 20° C. higher than the physiological temperature of the target tissues. In some embodiments, the duration and power density of the irradiation can be controlled by temperature probes 130 which monitor the tissue temperature. It should be noted that under certain conditions, non-ionizing radiation can result in thermal damage. Therefore, the maximum temperature is, in some embodiments, dependent on the duration of the irradiation. Accordingly, accurate control of the tissue temperature can be required under certain conditions or when particular types of radiation sources are utilized.

Subsequently or simultaneously with the emission of the non-ionizing radiation 118, the pulse generator 104 is configured to cause the plurality of voltage pulses to generated across electrodes 112, 114, to establish an electric field 122 through target tissues 120. At this point, the combined effect of temperature elevation and the voltage pulses causes cell death in the target tissues 120. Once the plurality of voltage pulses are no longer being, the radiation source 102 can be configured to discontinue operation.

In some configurations, the method above can be used with pharmacological or biological agents. Thus, while the plurality of voltage pulses are applied and the electric field is established, the pharmacological or biological agent can be introduced to the target tissues. Combined with the electroporation induced by the electric field, these agents can increase the lethality of the methodology described herein.

In the various embodiments, the operation of the radiation source 102 and the pulse generator needs to be synchronized to ensure that the temperature elevation does not occur after the plurality of pulses are applied. Otherwise, the treatment will be ineffective. Further, the pulse duration needs to be selected carefully, especially when higher temperatures are being used. As noted above, the temperature elevation can be as high as 20° C. above the physiological temperature. However, depending on the pulse duration, some Joule heating can occur and the temperature may be elevated beyond 20° C. Therefore, so as to not thermally affect the tissues via the pulses, the pulse duration needs to be short, especially when the radiation source is providing a high power density.

As shown in FIG. 1A, emitter 110 emits radiation 118 towards a general area of target tissues 120. However, such a configuration has several issues. First, since the direction of the radiation is not controlled, the temperature of healthy tissues may also be elevated. Thus, when the voltage pulses are applied, the resulting electric field could result in cell death of healthy tissues. Second, since the direction of the radiation is not controlled, energy is wasted on tissues outside the target tissues 120. Accordingly, the temperature elevation of the target tissues is performed in an inefficient manner. To alleviate such issues, system 100 can be modified to include additional elements to direct and focus the non-ionizing radiation on the target tissues. This is illustrated with respect to FIGS. 1B, 2, and 3.

Figure 1B:
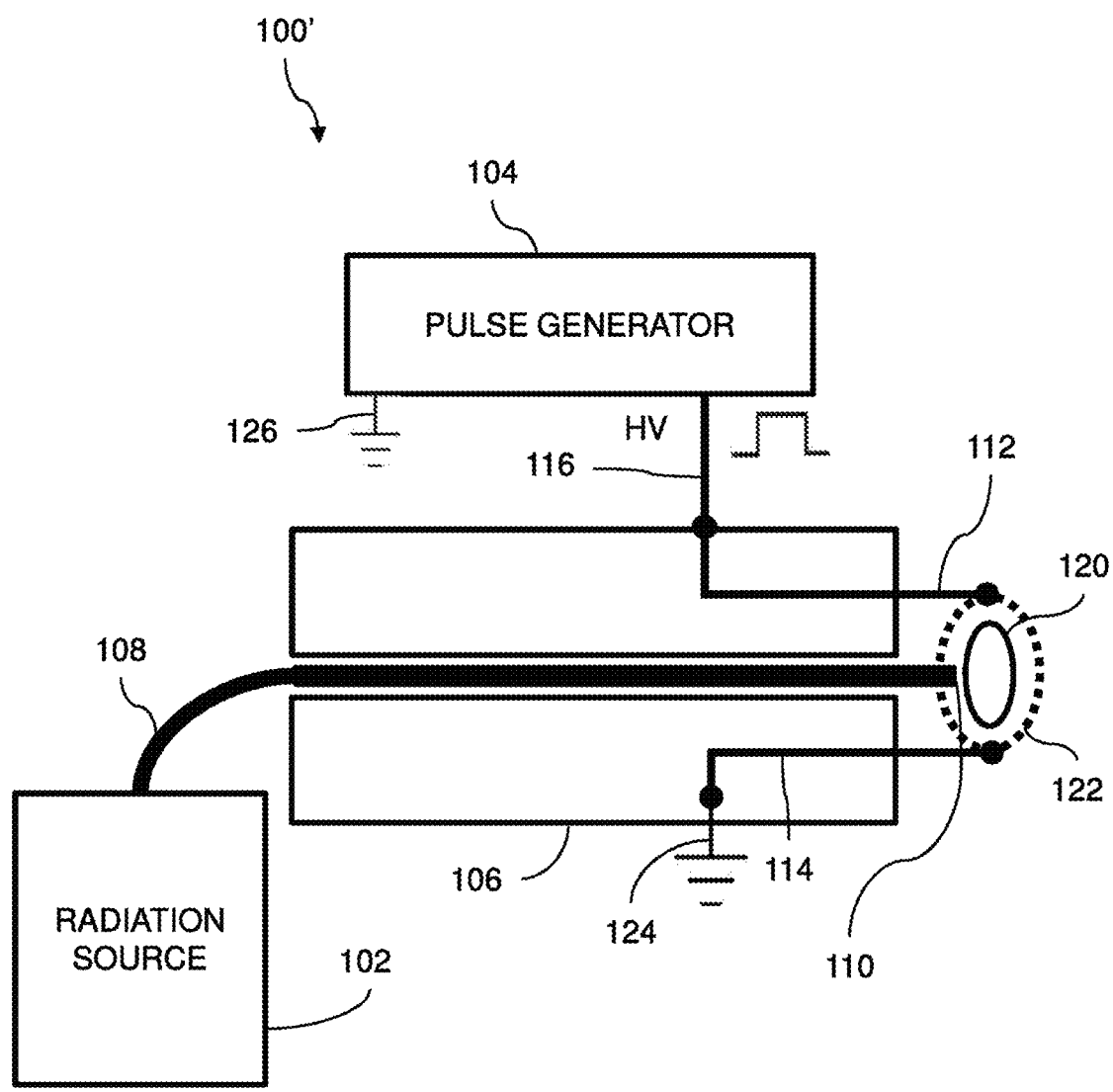
FIG. 1B is a schematic illustration of an alternate configuration for the system in FIG. 1A.

FIG. 1B is a schematic illustration of an alternate configuration for system 100 in FIG. 1A, denoted by system 100'. Some elements of system 100 have not been included in FIG. 1B for ease of illustration. However, system 100' can include any other elements shown in FIG. 1A.

As shown in FIG. 1A, the emitter 110 is substantially separated from target tissues 120. Thus, elevation of the temperature of target tissues relies on the radiation 118 reaching target tissues 120 with sufficient energy to elevate temperature. In contrast, FIG. 1B shows the emitter 110 at or nearly in contact with target tissues 120. Thus, any radiation from emitter 110 is provided directly to the target tissues.

In some embodiments all or part of the components of system 100 can be incorporated into a needle, catheter, laparoscopic probe, or other similar devices, that be inserted directly into the body of the subject. Such a configuration can be useful when the target tissues 120 are not surface tissues. Unfortunately, such a configuration can result in localized heating and limit the effectiveness of treatment, such as when the target tissues are large relative to the configuration of the emitter 110 and the electrodes 112 and 114. In such cases, such devices can include multiple emitters, electrodes, or both to ensure to cover a larger volume of the target tissues 120 and ensure such tissues are sufficiently elevated in temperature.

In some instances, the irradiation from emitter 110 may not provide effectively irradiate a volume of interest. For example, if the light source is collimated (e.g., as in a laser), the volume that can be illuminated or irradiated, and therefore heated, will be limited. In such cases a guiding or focusing device can be utilized to adjust the volume to be illuminated or irradiated. This is illustrated with respect to FIGS. 2A and 2B.

Figure 2A:
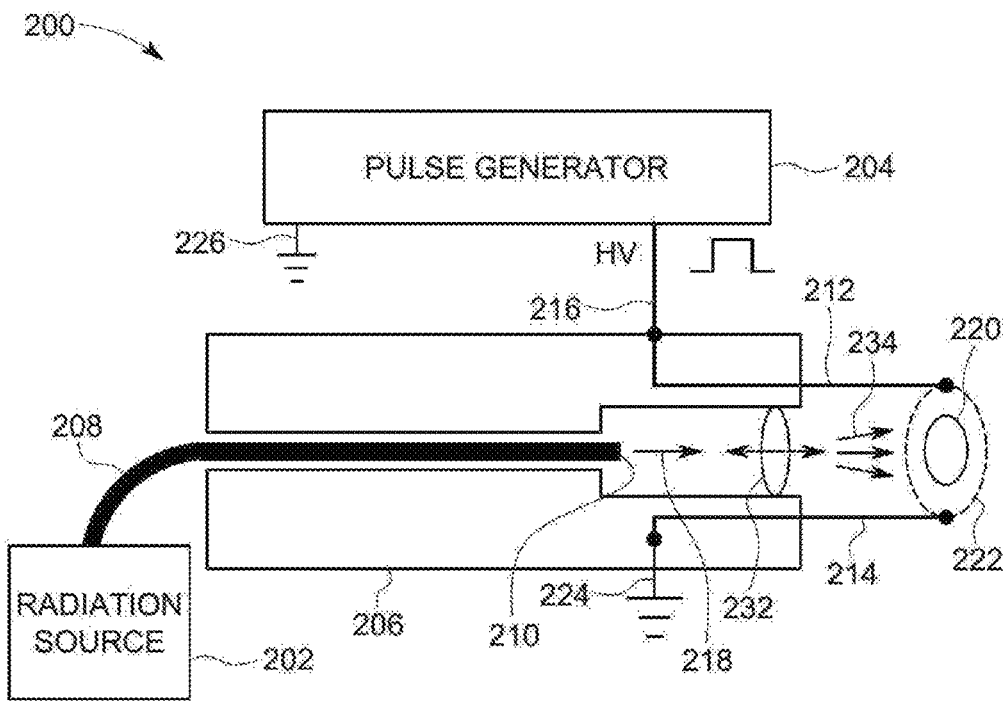
FIG. 2A is a schematic illustration of a system in accordance with an embodiment of the invention, incorporating a focusing lens.

FIG. 2A is a schematic illustration of a system 200 in accordance with an embodiment of the invention, incorporating a focusing lens 232 as a guide device. System 200 includes elements 202-226, which are substantially similar in configuration and operation to elements 102-126 in FIG. 1A. Accordingly, the description of elements 102-126 is sufficient for describing the configuration and operation of elements 202-226 in system 200 of FIG. 2A. Further, although FIG. 1A includes additional elements not shown in FIG. 2A, this is solely for ease of illustration and system 200 can include any other elements shown in FIG. 1A.

As noted above, one deficiency of the configuration of system 100 is the lack of control in volume that can be irradiated by radiation 118. In system 200, control is provided via focusing lens 232 provided in holder 206. In operation, the focusing lens 232 collects the radiation 218 from emitter 210 and provides redirected radiation 234 for target tissues 220. In the exemplary configuration of FIG. 2A, focusing lens 232 is shown as spreading out radiation 218 to produce a cone of redirected radiation 234 to illuminate or irradiate a larger volume. Alternatively, the focusing lens 232 can also be configured to focus radiation 218 at a single point or area of target tissues 220. In the case of microwave or millimeter wave radiation sources, such a configuration can be useful to enable irradiation of subsurface or deep tissues.

The result of the foregoing is that the radiation 218 can be directed to the target tissues 210 such that substantially all of the energy of radiation 218 is utilized to elevate the temperature of the target tissues 210 or a portion of interest therein. As a result, efficiency is increased, potentially allowing for a lower amount of power and energy to be used. Further, by focusing the radiation on the target tissues 220, the amount of healthy tissue damaged during treatment can be reduced.

Figure 2B:
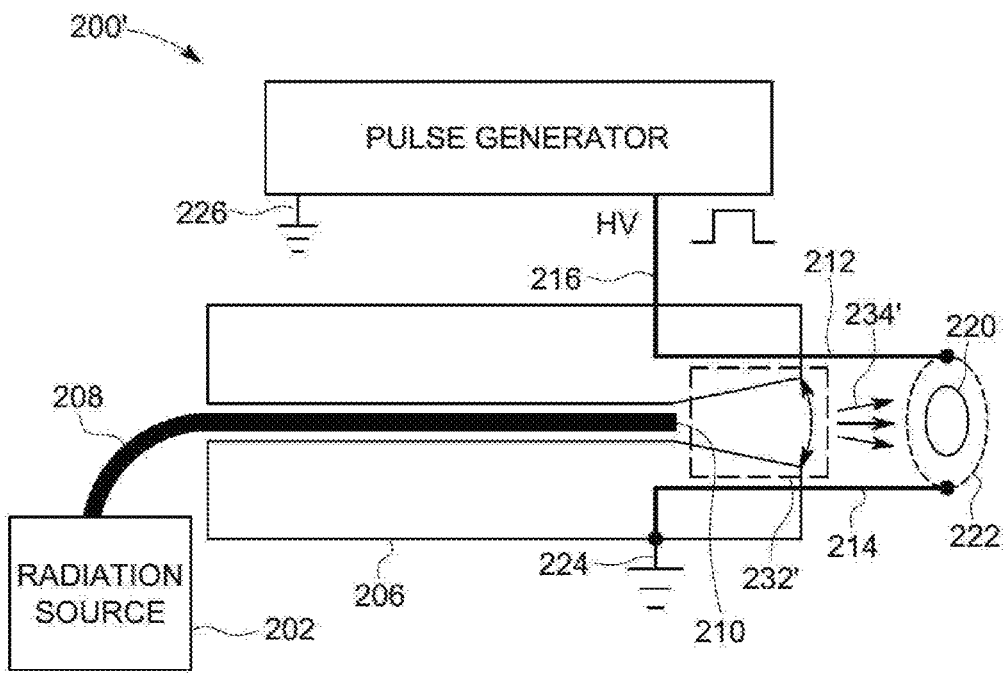
FIG. 2B is a schematic illustration of a system in accordance with an embodiment of the invention, incorporating mirror or reflector surfaces.

However, the various embodiments are not limited to focusing lenses and other guide devices can be used as well, such as mirrors, reflectors, waveguides, and optical fibers. This is illustrated with respect to FIG. 2B. FIG. 2B is a schematic illustration of a system 200', substantially similar to system 200, but incorporating mirror or reflector surfaces 232' instead of the focusing lens 232.

As in system 200, system 200' provides control of the spreading or focusing of radiation emitted from emitter 210. In system 200', control is provided via reflector surfaces 232' provided in holder 206. In operation, the reflector surface 332' redirects the radiation from emitter 210 and generates redirected radiation 234 for target tissues 320. In the exemplary configuration of FIG. 2B, reflector surfaces 232' are shown as generating a cone of radiation from the emitter 210 to produce the redirected radiation 234'. Alternatively, the reflector surface can also be configured to focus radiation from the emitter 210 at a single point or area of target tissues 220. Similar to the lens 232 in system 200, the reflector surfaces 232' of system 200' allow the radiation from the emitter 210 to be directed such that substantially all of the energy of the radiation from emitter 210 is utilized to elevate the temperature of the target tissues 220 or a portion of interest therein. Again, efficiency is increased, potentially allowing for a lower amount of power and energy to be used. Further, by focusing the radiation on the target tissues 220, the amount of healthy tissue damaged during treatment can again be reduced.

Further, systems 200 and 200' are not limited to only spreading or focusing of the radiation or to provide a fixed amount of spreading or focusing of the radiation. In some configurations, the arrangement of focusing lens 232 or reflective surfaces 232' can be adjustable, as shown in FIGS. 2A and 2B by the dashed arrows, to allow an operator to adjust the amount of spreading or focusing as required for different target tissues. Such adjustments are controlled manually by operator or can be controlled via control unit 128 or another control unit.

In some embodiments, a combination of methods can be used to direct the radiation from the emitter. That is, one or more lenses can be combined with one or more reflecting surfaces to provide directed radiation. The configured and number of elements can be selected based on the type of radiation, the size of the target tissues, and any other factors.

Although the embodiments described above are configured to provide a holder including most or all of the elements for carrying out the methods described herein, the various embodiments are not limited in this regard. That is, separate elements can be provided, as illustrated in FIG. 3.

Figure 3:
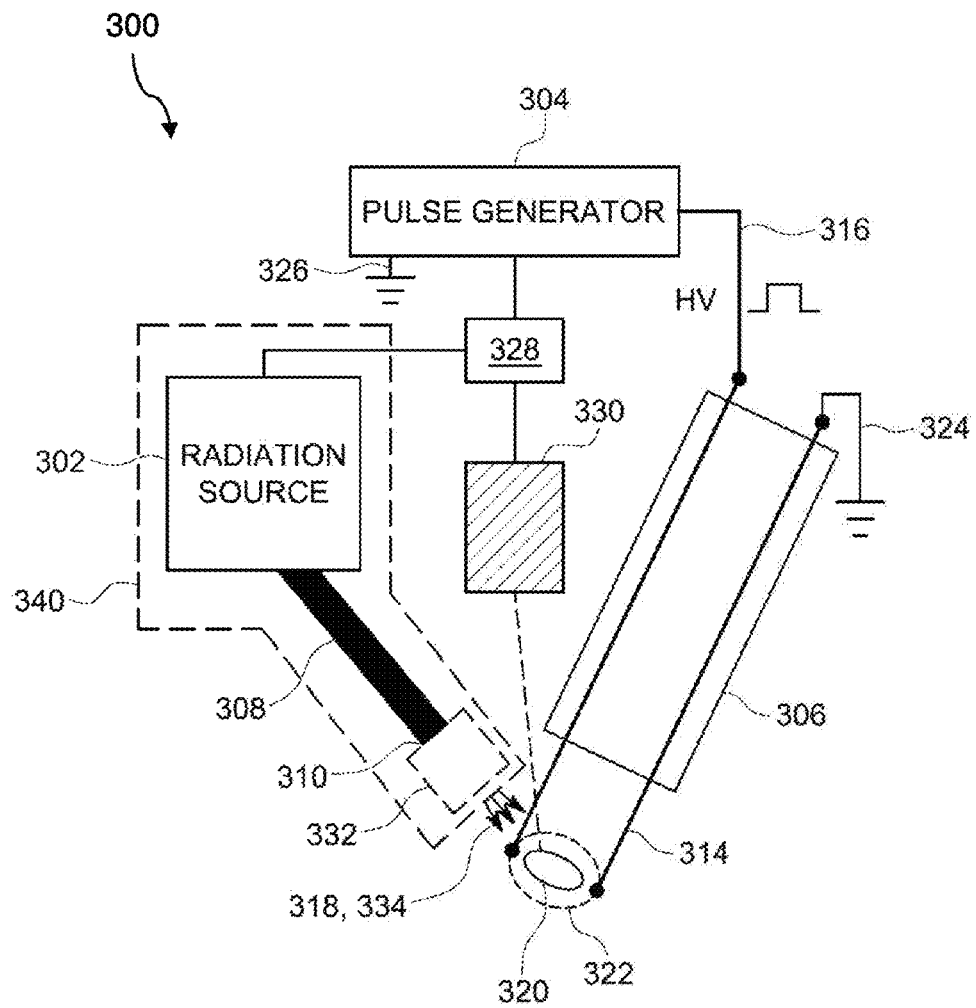
FIG. 3 is a schematic illustration of an alternate configuration for a system in accordance with the various embodiments.

FIG. 3 is a schematic illustration of a system 300 in accordance with an alternate embodiment of the invention. System 300 includes elements 302-332, which are substantially similar in configuration and operation to elements 102-126 in FIG. 1A. Accordingly, the description of elements 102-126 is sufficient for describing the configuration and operation of elements 302-326 in system 300 of FIG. 3. Further, although FIG. 1A includes additional elements not shown in FIG. 3, this is solely for ease of illustration and system 300 can include any other elements shown in FIG. 1A.

In system 300, rather than having a single holder incorporating the waveguide 308, the emitter 310, and the electrodes 312 and 314, as in system 100, the holder 306 in system 300 is configured for incorporating the electrodes 312 and 314. The illumination or irradiation of the target tissues 320 is provided by a separate illumination or radiation device 340, comprising radiation source 302, waveguide 308, and emitter 310. For example, device 340 can be a lamp, a standalone laser, or a standalone microwave or millimeter wave source, or any other device for generating radiation.

As in system 100, system 300 can include elements to provide control of the direction of radiation emitted from emitter 310. In system 300, control is provided via guide devices 332 between the device 340 and the target tissues 320, such as mirrors, reflectors, lenses, waveguides, optical fibers, and the like. As shown in FIG. 3, the guide devices 332 can be incorporated into device 340 or can be external to device 340.

In addition to the foregoing, a temperature probe 330 can be provided. As shown in in FIG. 3, the temperature probe 330 can be an optical probe or can be a contact probe, similar to the probe 130 in FIG. 1A. As shown in FIG. 3, the probe 330 can be a separate unit. Alternatively, the probe 330 can be incorporated into device 340 or holder 306.

In addition to the foregoing, the system 300 can include a control unit for coordinating operation of device 340 and pulse generator 304 based on a desired treatment scenario and the readings from probe 330.

In the exemplary configurations of the FIGS. 1A, 1B, 2A, 2B, and 3, each of these includes needle-type electrodes for producing electric fields. This produces electric field configurations similar to that of point charges. However, depending on the size of the target tissues such a configuration can be problematic. First, this results in a non-uniform electric field density across the target tissues. As a result, the effectiveness of the treatment will vary across the target tissues. Second, the non-uniform electric field density may cause damage to healthy tissues. That is, if healthy tissues are located a point at which the electric field density is particularly high, damage may occur, regardless of whether or not the temperature has been elevated. To alleviate such issues, system 100 can be modified to include other electrode arrangement types. This is illustrated with respect to FIG. 4.

Figure 4:
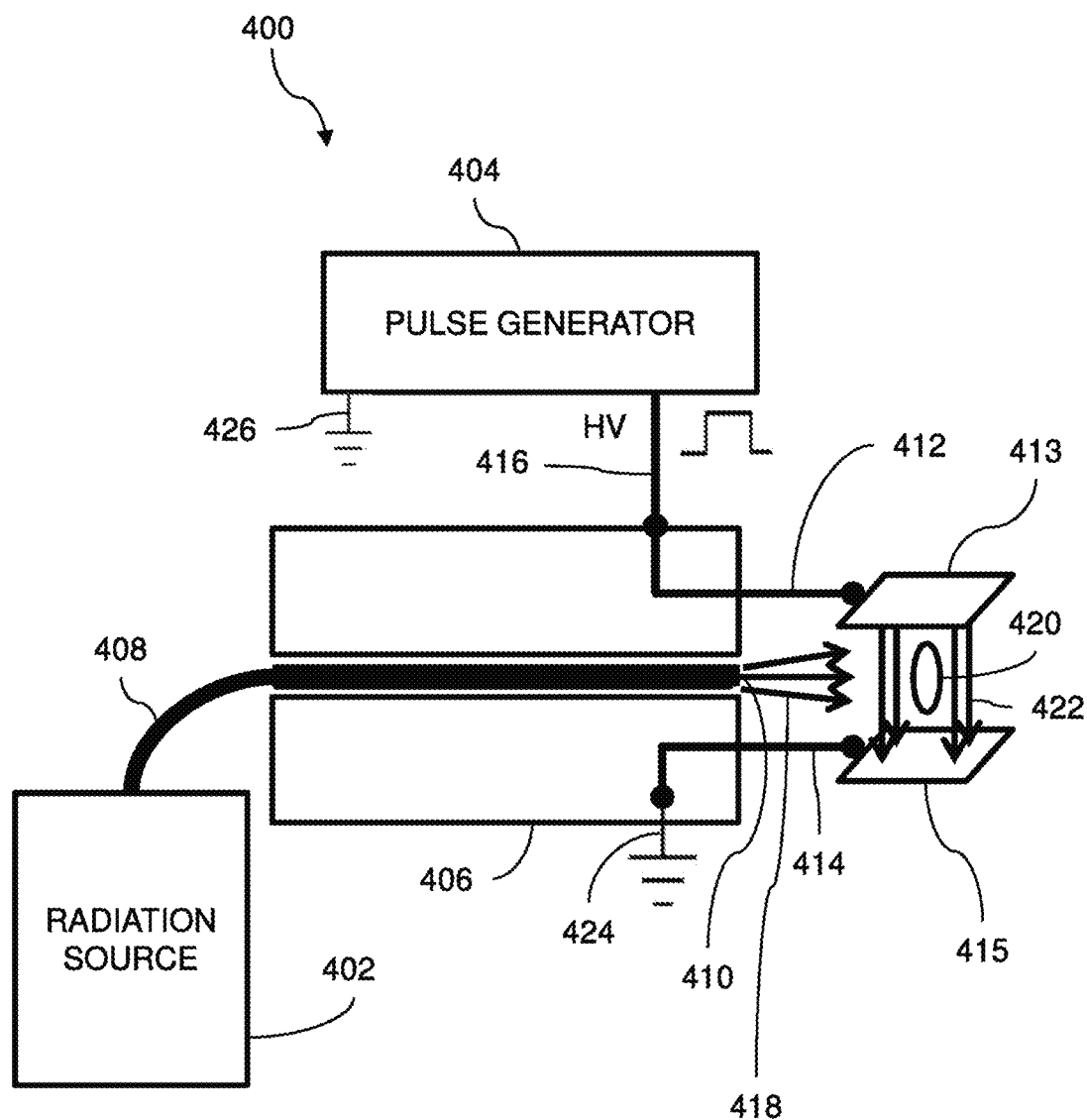
FIG. 4 is a schematic illustration of a system in accordance with an embodiment of the invention, incorporating plate electrodes.

FIG. 4 is a schematic illustration of a system 400 in accordance with an embodiment of the invention, incorporating plate electrodes 413 and 415. System 400 includes elements 402-426, which are substantially similar in configuration and operation to elements 102-126 in FIG. 1A. Accordingly, the description of elements 102-126 is sufficient for describing the configuration and operation of elements 402-426 in system 400 of FIG. 4. Further, although FIG. 1A includes additional elements not shown in FIG. 4, this is solely for ease of illustration and system 400 can include any other elements shown in FIG. 1A.

In order to provide a more uniform electric field density, system 400 incorporates a pair of parallel, flat plate electrodes 413 and 415, facing each other and coupled to electrodes 412 and 414, respectively. Thus, when a voltage is applied across electrode 412 and 414, the resulting electric field 422 between electrode 413 and 415 is substantially uniform in density with respect to the target tissues 420. Thus, the increased control of the treatment is provided.

In the exemplary configurations of FIGS. 1A, 1B, 2A, 2B, 3, and 4, each is shown with a first electrode and a second counter-electrode. However, the various embodiments are not limited in this regard. Rather any number of electrodes can be utilized. Further, any electrode geometry can be utilized as well. For example, a mix of plate and needle-type electrodes can be used. In another example, the electrode plates can be non-parallel, non-flat, or both.

EXAMPLES

The examples shown here are not intended to limit the various embodiments. Rather they are presented solely for illustrative purposes.

To illustrate the concepts above, effect of subnanosecond electric field pulses on mammalian cells (liver cancer cells) at elevated temperatures was studied, with temperatures above room temperature (25° C.) extending to 47° C. The temperature increase due to Joule heating has been kept at values small compared to the externally provided thermal energy, which allowed the temperature to be varied independently of the specific electrical energy. The specific electrical energy, W, or specific energy in short, is defined as the total electric energy expenditure per unit volume. For N square wave pulses it is:

$$W = E_o^2 \cdot \sigma \cdot \tau \cdot N \quad (1)$$

in which $E_o$ is the applied electric field, $\sigma$ is the conductivity of the medium, and $\tau$ is the pulse width.

Trypan blue exclusion assay was used as an indicator of plasma membrane integrity and of cell viability. Trypan blue is normally impermeant to healthy cells. When cell membrane integrity is compromised, this dye is able to enter the cell and bind to protein, making the cell appear blue. Cells that take up this dye several hours after exposure to electrical pulses are usually considered dead or dying. The measured Trypan blue uptake by the cells was measured 4 hours after exposure to pulses.

For purposes of the study, the pulse width was kept constant at 200 ps, and the electric field was varied from 52 kV/cm to 95 kV/cm. In order to determine the temperature effect on permittivity and conductivity, which results in changing the electric field distribution across the cell membrane and energy transfer into the cell, particularly into the cell membrane, the electrical characteristics of the cell were measured using dielectric spectroscopy. The effect of increased temperature on pore formation in the cell membrane was modeled by means of molecular dynamic simulations.

Materials and Methods

Pulse Generator

The design of the pulse generator used for these experiments is based on a design described in references [8] and [13]. A Marx Bank with 8 stages, each one with a capacitance of 2.3 nF, was used to generate up to a 20 kV pulse. The Marx Bank was discharged into the load containing the biological sample by means of an atmospheric pressure spark gap switch. The resulting pulse has a risetime of 150 ps. A tailcut switch was used to shorten the pulse duration to 200 ps. Both switches were integrated in the 3 m long, 50 Ω cable (RG217-U) between the Marx Bank and the load. In order to insure minimum reflection, the sample chamber (exposure chamber) was designed to ensure an impedance as close as possible to 50 Ω while providing a homogeneous electric field across a sample of sufficient volume.

Exposure Chamber

The load consists of a biological sample which was placed in an exposure chamber between disc shaped electrodes made of stainless steel. The exposure chamber was designed to provide a uniform electric field between 50 kV/cm and 120 kV/cm across the biological sample at pulse amplitudes ranging from 10 kV to 20 kV. The electrode separation in the chamber was consequently, 1.8 mm. In order to provide a sample volume of 30 μL, a minimum volume required for the biological analysis, the radius of the electrodes must exceed 2.3 mm. A radius of 2.4 mm was chosen which resulted in a sample volume of 32.5 μL.

The conductivity and the permittivity of the medium (complete medium containing Dulbecco's Modification of Eagle's Medium (Cellgro, Fisher Scientific cat#10-013-CV) supplemented with 10% FBS (Cellgro, Fisher Scientific cat# 35-015-CV) which was used for the cell suspension was measured by means of Time Domain Dielectric Spectroscopy at frequencies of 100 MHz and 1 MHz, respectively for varying temperatures (Table 1). Assuming that the electrical parameters of the medium are identical to the cell suspension, a reasonable assumption considering the relatively small concentration of cells in the medium (2.5%), these values were used to calculate the resistance and capacitance of the sample. With a conductivity of 1.37 S/m and a relative permittivity of 79.3 at room temperature (25° C.), the sample resistance and capacitance was calculated as 72.6 Ω, and 7 pF, respectively. However, since the gap distance in our case is comparable to the electrode radius the standard equation for parallel-plate capacitors, which we have used, needs to be modified in order to take the fringe fields into account. This would result in a slightly smaller value of the capacitance.

TABLE 1

Permittivity and conductivity of the medium used for the cell suspension depending on temperature. Also listed is the resulting capacitance and resistance of the sample.
Electrical Parameters of the Medium in the Chamber

| T (° C.) | Permittivity | Conductivity [S/m] | C [pF] | R [Ω] |
|---|---|---|---|---|
| 25 | 79.3 | 1.37 | 7 | 72.6 |
| 37 | 72.7 | 1.74 | 6.7 | 57.2 |
| 42 | 67.6 | 1.88 | 6 | 53 |
| 47 | 64.1 | 2.03 | 5.7 | 49 |

Figure 5:
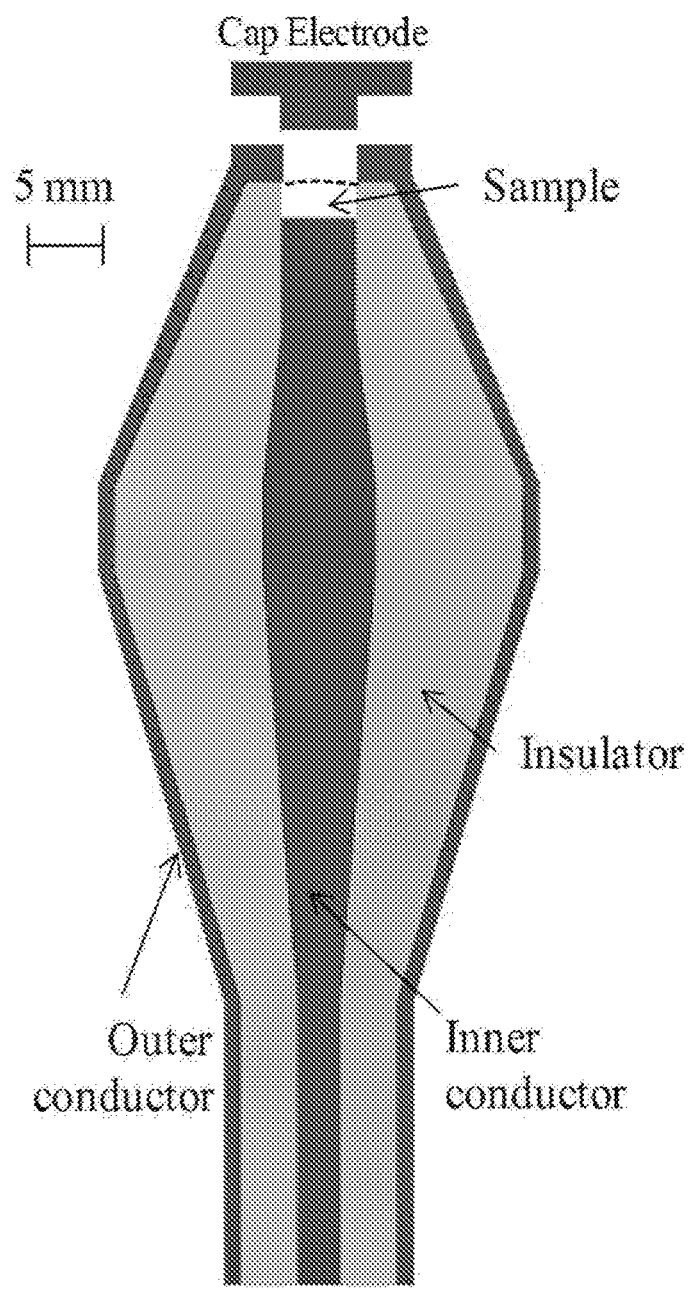
FIG. 5 shows schematics of the connector between high voltage cable and exposure chamber.

Since the radius of the sample (2.4 mm) is larger than the radius of the inner conductor (1.34 mm) of the 50 Ω cable which connects to the chamber, a coaxial waveguide was designed and built (as shown in FIG. 5) which expanded the inner conductor to the electrode diameter of the exposure chamber, while maintaining the 50 Ω impedance over the entire length from the cable to the chamber. The dielectric between the inner and outer conductor was polypropylene with a permittivity of 2.38, the same as that of cable. The shape of the waveguide, with its conical shape at the chamber, is such that it allows a rather smooth transition from the transverse electric fields in the cable to the axial electric field in the sample.

Figure 6:
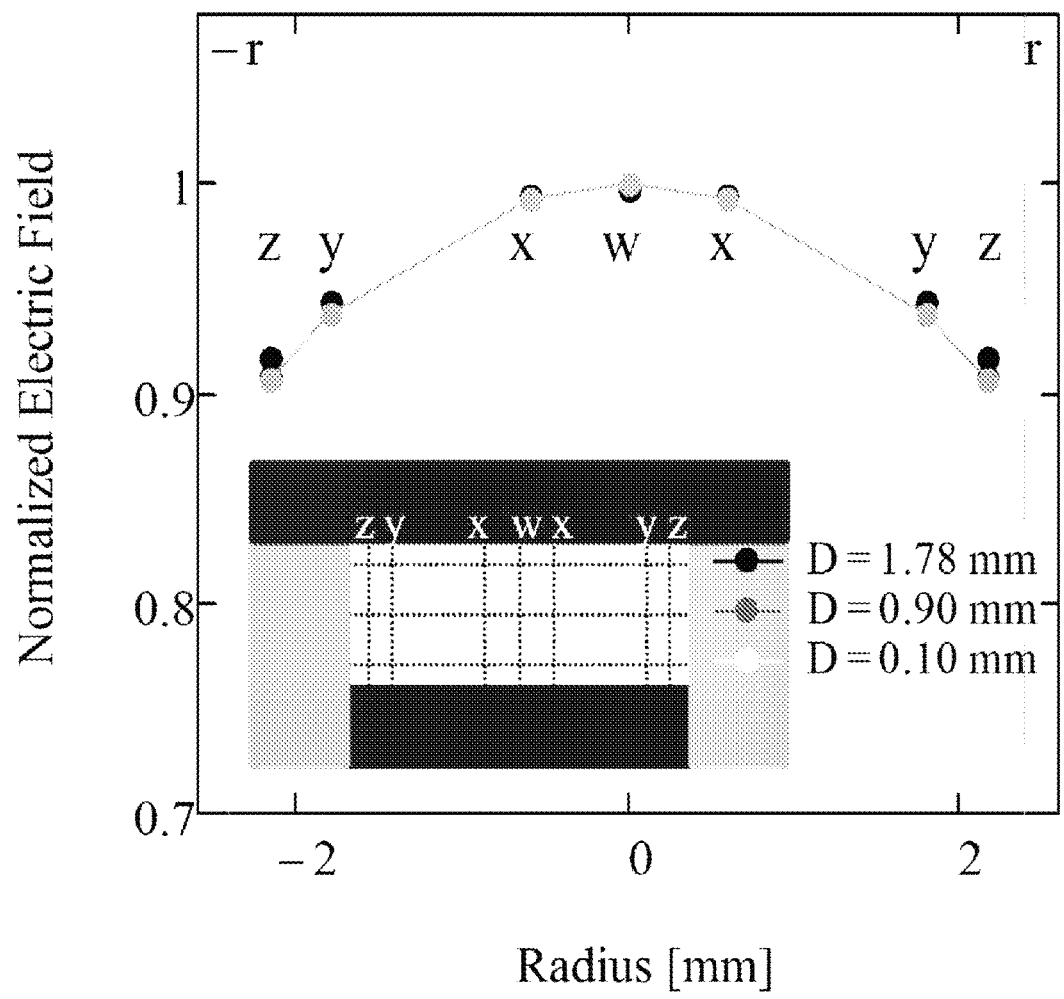
FIG. 6 shows simulation results of the electric field strength in the sample for the configuration of FIG. 5.

In order to determine the distribution of the electric field within the sample, a three-dimensional, time dependent electromagnetic field solver (MAGIC) was used. A description of the use of MAGIC for these types of simulations is discussed in reference [15]. A voltage pulse of 200 ps with an amplitude of 10 kV was used in the simulation. The axial electric field was calculated from the high voltage electrode to the ground electrode (0 mm-1.8 mm) and from the inner radius to the outer radius (0 mm-2.4 mm). The results are shown in FIG. 6. The insert in FIG. 6 is the enlarged exposure chamber (shown in white) between the two electrodes (shown in black). The letters (w, x, y, z) represent the radial positions, at which three axial positions at D=0.1 mm, 0.9 mm, and 1.78 mm between the electrodes, the electric field values shown in FIG. 2 were obtained. The radial distribution of the axial component of the electric field is shown for three axial positions. The radial component of the electric field, which was also calculated, was found to be very small compared to the axial component of the field strength, and was therefore neglected in the data shown in FIG. 6. The results show a good homogeneity in the axial direction with less than a 1.5% deviation. The electric field is less homogeneous in radial direction. It decreases from the center to the outer radius of the sample by 9.4%.

Electrical Diagnostics

The voltage is measured with a capacitive voltage divider 9.23 cm in front of the load (4.5 cm from end of cable) within the cable. In order to obtain an accurate voltage measurement, the time constant of the probe ($R_p \cdot C_t$) must be very large compared to the pulse width (200 ps), where $C_t$ is the series capacitance of the probe, and $R_p$ is the damping resistance. To satisfy this condition, the resistive value of $R_p$ was chosen to be 2.3 kΩ, which gives a time constant of 8.3 ns.

Two techniques were used to calibrate the voltage probe. The first technique used a known pulse from a low voltage (<1 kV) FID pulse generator FPG 5-P (FID GmbH, Germany). The voltage ratio was found to be 3220. The second technique, as described in reference [13], is based on discharging a 10 cm cable at a defined voltage into a matched load. The charging voltage was compared to the voltage pulse obtained with the capacitive voltage divider probe. For a matched load, the amplitude of the pulse obtained from the capacitive divider probe is half of the charging voltage. This method provided a value of 3170 as the voltage divider ratio, which is close to the value obtained with the first calibration technique. The average of the two values (3200) was used to determine the voltage.

The capacitive probe is connected to the oscilloscope by a 3 meter 50 Ω cable (RG58), and a 20 dB, SMA attenuator (PE7045-20). The frequency response of the cable and the attenuator was measured using an 8753E 3 GHz network analyzer. As the frequency was increased to 3 GHz, the change in the impedance of the system was found to be negligible.

The probe was placed as close to the load as possible, but at a distance which still allowed us to separate the incoming from the reflected pulse. With the probe placed 4.5 cm from the end of the cable at the connector to the exposure chamber, and the length of the connector being 4.7 cm, at a relative permittivity of the dielectric of 2.38, the roundtrip time of the pulse from probe to exposure chamber and back is equal to 0.95 ns. This time corresponds to the temporal separation of incoming to reflected pulse.

Voltage Measurements

Although the resistance of the sample at room temperature (72.6Ω) exceeds the impedance of the cable and waveguide (50Ω), the relatively large capacitance of the exposure chamber, determined by the high permittivity of the medium, results in a reduction of the voltage across the load, V(t). The incoming signal, $V_{in}(t)$, that is seen by the load can be determined by recording the signals for the case of the load being infinite, $V_{open}(t)$, and zero, $V_{short}(t)$. With $$V_{open}(t)=V_{in}(t)+u(t)\cdot V_{in}(t) \quad (2a)$$

and $$V_{short}(t)=V_{in}(t)-u(t)\cdot V_{in}(t)V_{short}(t)=V_{in}(t)-u(t)\cdot V_{in}(t), \quad (2b)$$

where τ is the roundtrip time of the pulse from voltage probe to load and back, and u(τ) is a step function at the time τ. The voltage of the incoming pulse can then be calculated as:

$$V_{in}(t)=[V_{open}(t)+V_{short}(t)]/2\cdot V_{in}(t)=[V_{open}(t)+V_{short}(t)]/2 \quad (3)$$

Figure 7A:
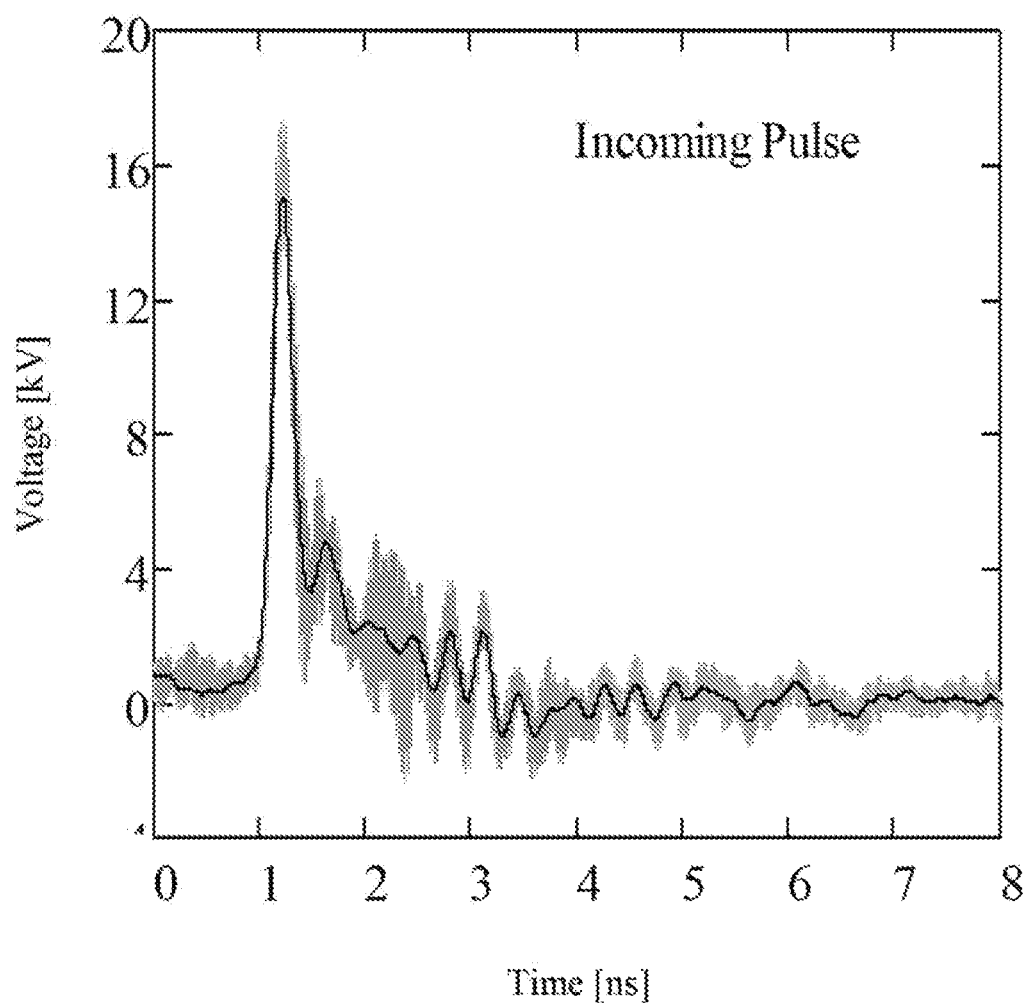
FIG. 7A shows the average incoming signal, with an amplitude of 15 kV, measured in front of the exposure chamber (black trace) displayed over an envelope of 100 pulses.
Figure 7B:
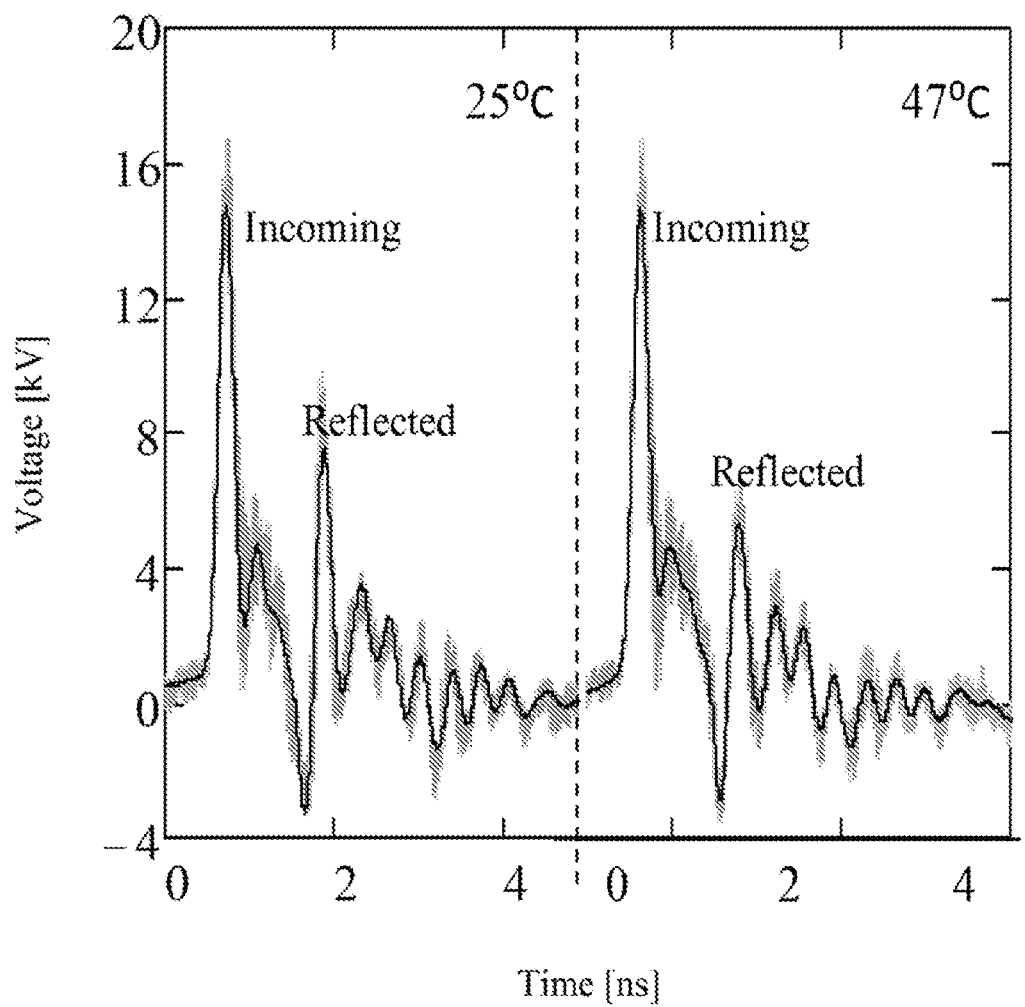
FIG. 7B shows the average voltage measured 9.23 cm in front of the load at 25° C. and 47° C.
Figure 7C:
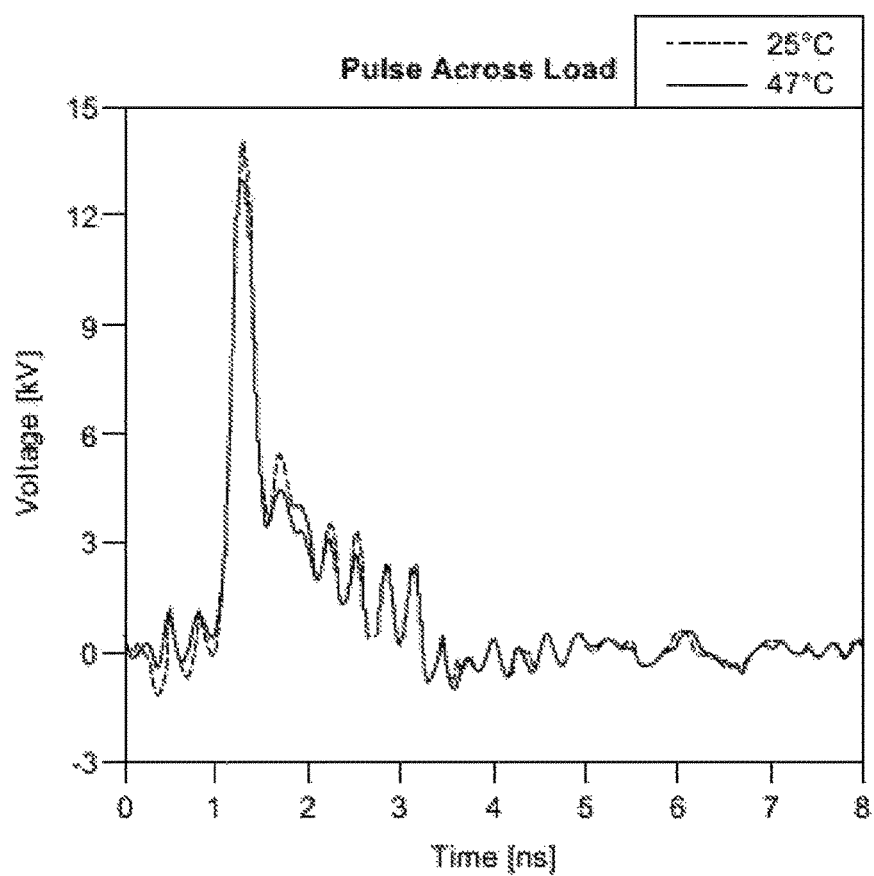
FIG. 7C shows the voltage across the load at a temperature of 25° C. and 47° C.

FIG. 7A shows the average incoming signal, with an amplitude of 15 kV, measured in front of the exposure chamber (black trace) displayed over an envelope of 100 pulses. FIG. 7B shows the average voltage measured 9.23 cm in front of the load at 25° C. and 47° C. The traces show clearly the temporal delay of the reflected to the incoming pulse. FIG. 7C shows the voltage across the load at a temperature of 25° C. and 47° C. The amplitude of the pulse is 14 kV and 13 kV for 25° C. and 47° C., respectively.

The solid black trace in FIG. 7A is the derived voltage trace ($V_{in}(t)$) determined from (3). It shows a voltage pulse with a FWHM of 200 ps, and amplitude of 15 kV followed by a series of pulses with decreasing amplitude. The gray represents an envelope of 100 pulses. From the spread in voltage the deviation from an average value is estimated to be approximately ±9%. The reflected voltage pulse, $V_{ref}(t)$, can then be determined by subtracting the calculated incoming pulse voltage, $V_{in}(t)$, from the measured voltage, $V_m(t)$, with the load being the biological sample.

The measured voltage 9.23 cm in front of the load, recorded at sample temperatures of 25° C. and 47° C., is shown in FIG. 7B. The reflected pulse, which is superimposed to the incoming pulse, is delayed by 0.95 ns with respect to the incoming pulse, in accordance with the roundtrip time of the pulse. By shifting the reflected pulse by the measured delay time toward the incoming pulse and superimposing the two pulses the voltage across the load can be determined. This is shown in FIG. 7C for two temperatures, 25° C. and 47° C. For 25° C. the amplitude of the voltage across the load is 7% lower than the amplitude of the pulse measured with the capacitive voltage divider. With increasing temperature the difference between measured voltage and actual voltage across the load increases to 11% for 37° C. For 42° C. and 47° C. the difference in amplitudes are increased to 12% and 13%, respectively. The pulse voltage computed with P-Spice, a circuit solver, and with the load impedance based on the data in Table 1, corrected for the capacitance, showed the same tendency as that of the measured pulses with respect to temperature.

Temperature Control

In order to heat the sample externally, the exposure chamber was placed into an insulated box (1 m×0.5 m×0.5 m) in which the interior was heated with a heat gun. Once the interior of the box reached the desired temperature, the power of the heat gun was decreased in order to maintain the temperature. The sample was then placed within the chamber, and given 1 minute to reach the ambient temperature. Based on the temperature studies described in the following, this time is more than sufficient for the sample to achieve temperature equilibrium with its environment.

Figure 8:
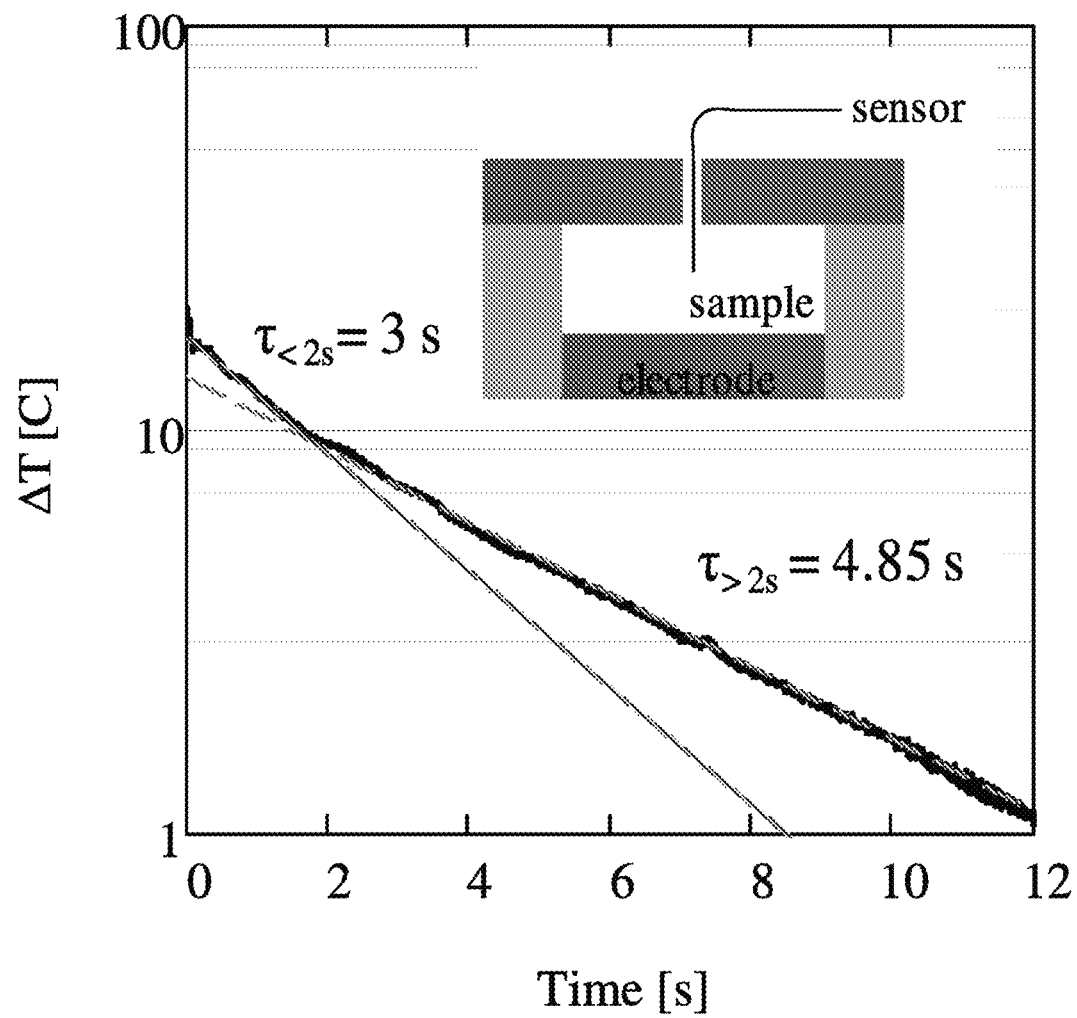
FIG. 8 shows the measured thermal decay time constant (bold) of the exposure chamber.

The temperature of the sample was not measured directly due to fact that there was no access through the ground electrode, but indirectly by measuring the temperature of the conductive cap placed over the sample with a fiber optic temperature sensor (Neoptix, T1S-11854A). However, in order to determine the time needed for the temperature of the sample to reach the temperature of the chamber, or how much the temperature of the sample is increased during pulsing, the thermal decay constant was measured. This was achieved by placing a sample, heated to 50° C., into the chamber and placing a cap which held the 30 μm diameter optical sensor (FISO: FOT-HERO, resolution: 0.03° C.) over the sample, as depicted in FIG. 8. FIG. 8 shows the measured thermal decay time constant (bold) of the exposure chamber. The temperature of the sample by the time the probe was placed in the exposure chamber was 40° C. and it decayed to 23° C. The initial thermal decay time constant (<2 s) was measured to be 3 seconds, while it was increased to 4.85 seconds at times above 2 s.

The initial temperature decay has a thermal constant of 3 s, while the thermal decay time constant after 2 seconds is equal to 4.85 seconds. The fast decay is determined by the initial rapid decay of the temperature at the electrodes, which causes the build-up of a temperature gradient from the center of the sample to the electrodes. The decay during this phase is determined more by the thermal properties of the medium rather than by the thermal conductivity of the metal electrodes. From the measured thermal decay, it was determined that 1 minute was sufficient time between the placement of the sample in the chamber and the start of the pulsing to allow the temperature of the sample to reach the ambient temperature.

The temperature of the sample will increase as a result of the pulsed electric fields until Joule heating and thermal losses mainly due to heat conduction, balance out. This equilibrium temperature is known as the leveling temperature, which is derived from Newton's law of cooling:

$$T_{Level} = T_i + \frac{dT}{1-e^{-1/\tau_{th}\cdot f_r}} \cdot T_{level} = T_i + \frac{dT}{1-e^{-1/\tau_{th}\cdot f_r}} \quad (4)$$

The thermal decay time constant, $\tau_{th}$, for pulses with repetition rates exceeding f=0.5 pps (½ s), is determined by the initial, rapid decay in temperature. With a pulse repetition rate of 10 pps, the relevant time constant is 3 s. The energy of a single, 200 ps pulse of amplitude 30 kV into a 72Ω load is equal to 2.5 mJ, which equates to a temperature increase of 0.018° C. per pulse (dT). The leveling temperature ($T_{level}$) was calculated to be 23.55° C., with an initial temperature ($T_i$) of 23° C., which equates to a temperature increase of 0.55° C. It is therefore safe to assume that Joule heating under the conditions of our experiment can be neglected compared to heating with the external source.

In order to determine the effect of temperature alone, without pulsing, experiments were performed using a water-bath which could be heated quickly, i.e,, in about one minute. One hundred fifteen microliter of Hepa 1-6 cells at a concentration of 6 million cells/ml were placed at the bottom of 1.5 ml polypropylene centrifuge tubes, which were dipped in water bath (GCA Precision, model # Thelco 183) for 1, 2, 5, 10, 15, 30 and 105 minutes at 42° C., 47° C. or 52° C. The temperature of the water bath was measured using a standard mercury thermometer. The temperature in the centrifuge tubes were monitored by an optical temperature probe. The time it takes for the temperature to reach 47° C. is approximately 1 minute, longer than for the heating method described above. After water bath incubation the cell tubes were immediately transferred to a 37° C. tissue culture incubator (NUAIRE, model# NU-8700) and incubated or "recovered" for 4 more hours. The cells were then assessed by the Trypan blue exclusion assay as described earlier except the cells were diluted in 0.4% Trypan blue solution at a 1:8 ratio.

Cell Culture and Trypan Blue Exclusion Assay

The mouse hepatoma epithelial cell line (Hepa 1-6) was obtained from American Type Culture Collection (ACCT, Manassas, Va.) and cultured in complete medium containing Dulbecco's Modification of Eagle's Medium (Cellgro, Fisher Scientific cat# 10-013-CV) supplemented with 10% FBS (Cellgro, Fisher Scientific cat# 35-015-CV). The passage number of the cell line used in the experiments did not exceed 20.

To prepare for the experiment, Hepa 1-6 cells at 80-90% confluency in tissue culture flasks were washed with PBS (Cellgro, Fisher Scientific cat# 21-040-CV) at room temperature and treated with trypsin-EDTA (Cellgro, Fisher Scientific cat# 25-053-C1) at 37° C. for 5 minutes. The trypsinized cell suspension was neutralized with a 4 times equivalent volume of complete medium and centrifuged at 100 g for 10 minutes, followed by the removal of the supernatant. The cells were resuspended in complete medium and counted by Trypan blue exclusion assay on the hemocytometer (Fisher Scientific cat# 02-671-54) under the microscope with the final concentration of 0.2% Trypan blue. The use of a proper volume of resuspension medium ensures that every 16-square area on the hemocytometer contains 50-100 cells (200-400 cells in 4 areas). Cell viability, which equals the percentage of live cells among the total number of cells, was calculated. Then the required number of cells was transferred to a new tube, centrifuged and resuspended in an appropriate volume of complete medium to make a final concentration of 6 million cells per ml for downstream experiments.

The Trypan blue exclusion assay was used as an indicator of plasma membrane integrity and of cell viability after pulse exposure (4 hours later). The exposure chamber was filled with 35 µL of the sample. Care was taken to make sure that the chamber was filled to prevent any air gap between the sample and the top electrode (cap electrode). By monitoring the voltage across the sample, which, in the case of air gaps, would have shown deviations in shape and amplitude from that expected for samples with good contacts to the electrodes, we made sure that the voltage was always applied across the sample at the beginning and during pulsing. After exposure, 30 µL of the sample was removed from the chamber and placed in a vial with 40 µL of medium (same medium used for culturing), thus decreasing the cell concentration to approximately 2.6·106 cells/mL. The cells were incubated for 4 hours at 37° C. until they were examined for viability. The same technique of Trypan blue exclusion assay described earlier was used, except the total cells counted were between 400 and 500 cells for each data point. The sham treated cells underwent the same procedures as the exposed cells, but without experimental exposure to the electric pulses.

Experimental Protocol

Before experiments, a heat gun was used to raise the temperature of the chamber for approximately 30 minutes to the desired temperature (37° C., 42° C. or 47° C.). Once the temperature was reached, the power of the heat gun was reduced to maintain the temperature. Thirty-five µL of the sample was placed into the chamber for 1 minute to allow the temperature of the sample to equilibrate to the ambient temperature of the chamber. Pulses were applied at a rate of 7-9 pps, and 30 µL of the sample was removed from the chamber and placed into a vial with 40 µL of the growth media. The control sample underwent the same procedure, but without applying the pulsed electric fields (sham). The vials containing the samples were covered with mylar tape, and placed in an incubator for 4 hours at 37° C. After 4 hours, the vials were removed from the incubator, and the samples were examined by Trypan blue uptake at a 1:1 ratio.

For the membrane permeability experiments, 17 µL of Trypan blue were mixed with 18 µL of sample and placed into the exposure chamber to undergo the experimental conditions. After exposure, 30 µL of the mixed sample was placed in 40 µL of solution containing 20 µL of Trypan blue and 20 µL of culture medium. Cells were examined for Trypan blue uptake immediately afterwards.

Measurements of the Electrical Properties of Cells by Means of Dielectric Spectroscopy In order to measure the conductivity and permittivity of the cell, Time Domain Reflectometry (TDR) Dielectric Spectroscopy analysis was applied, as described in reference [18]. An Agilent 86100C TDR oscilloscope was used together with a 54754A differential plug-in. A cutoff type coaxial termination-sensor with gold-plated stainless steel electrodes was used to hold cell suspensions of 50 µl with a 10% volume fraction of cells. In order to minimize the effect of electrode polarization, the cells were suspended in a low conductivity buffer as suggested by previous studies. The incident voltage pulse is generated by the differential plug-in with 35-ps rise time and 200-mV amplitude. The same module also receives the reflected signal with an 18-GHz detection bandwidth. The temperature was controlled by immersing the sensor in a water bath with a thermostat (Julabo, San Diego, Calif.). The complex permittivity of the sample was calculated by performing a Laplace transform on the incident and reflected signals as suggested by Hager in reference [18]. The relative permittivity and conductivity of the sample was further determined from the complex permittivity. After correction for electrode polarization, the permittivity and conductivity spectra of the cell suspension were fitted based on a combination of the Maxwell-Wagner mixture model and a single-shell cell dielectric model for the known size and membrane thickness of cells. Dielectric parameters for each cellular component, such as the membrane and the cytoplasm, can then be determined from the fit.

Molecular Dynamics Simulation Approach

Simulation studies of membrane electroporation under a constant applied voltage were carried out as an example of a bio-process affected by both the electric field and temperature. The poration process was modeled through atomistic Molecular Dynamic (MD) simulations. This MD technique allows for the simulation of a membrane patch from which one can ascertain whether pore formation can occur within a certain time at a chosen value of external field and fixed temperature. The GROMACS package, as described in references [19] and [20] was used for the MD simulations of membrane effects at different temperatures. The GRO- MACS tool provides the force fields for the lipid membrane, which was assumed to comprise dipalmitoyl-phosphatidyl-choline (DPPC) molecules. The Simple Point Charge (SPC) water model mimicked the aqueous environment surrounding the membrane. Velocities of water and membrane molecules were generated randomly at each simulation run according to a Maxwellian distribution. For statistical significance, a total of eight MD simulations were carried out with different starting molecular velocities for each case. A 4 fs time step was used.

Results

Effect of Temperature without Pulse Application

Figure 9:
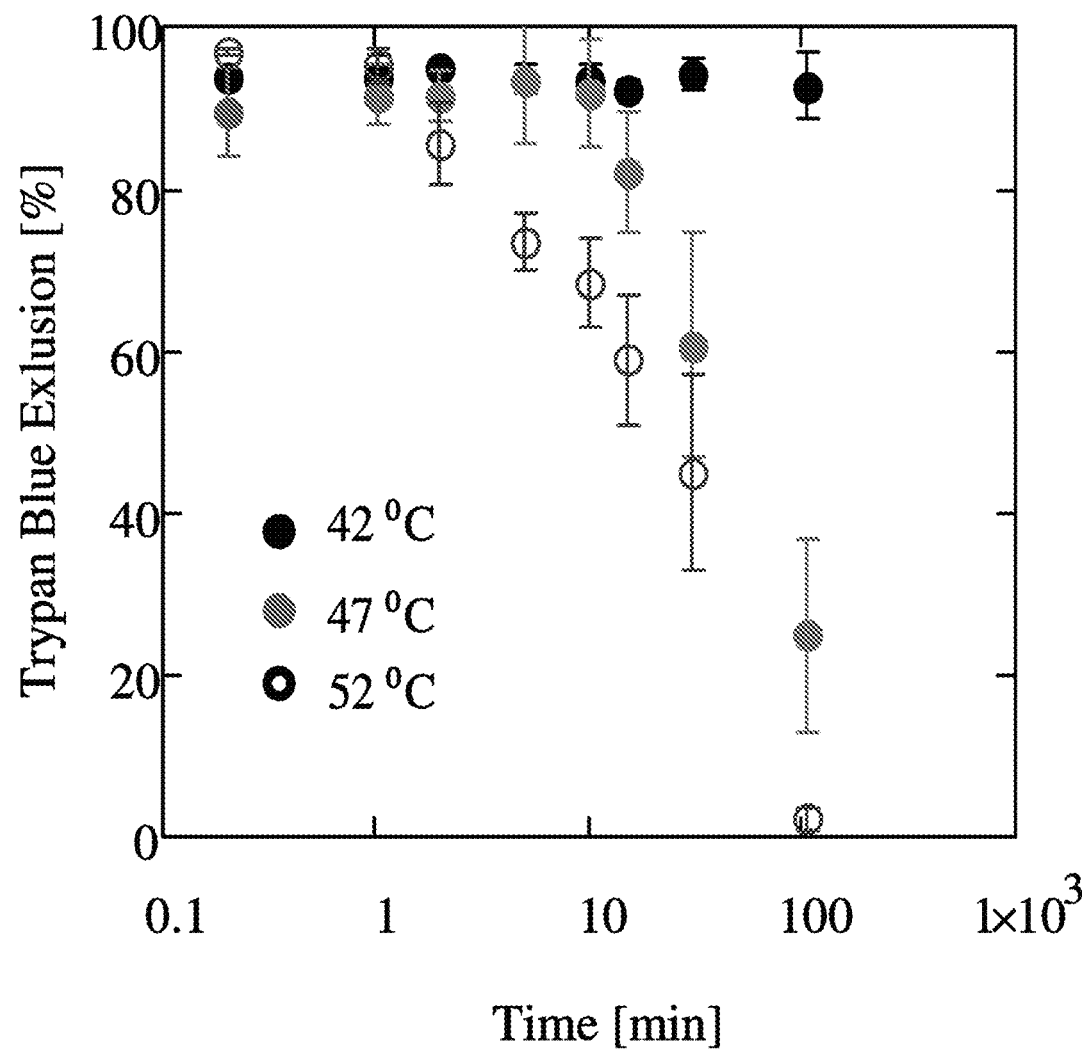
FIG. 9 shows Trypan blue exclusion versus exposure time of cells placed in a water bath of 42° C., 47° C. and 52° C.

In order to determine the effect of temperature alone, i.e., without pulsing, experiments were performed using a water-bath. It could be heated within times similar to those used in the heating system where a heat gun was used to increase the ambient temperature. That is, it takes about 1 minute for the temperature of the sample in the water bath to reach 47° C., which is on the same order as required using the heat gun. Three independent experiments were conducted for temperatures of 42° C., 47° C. and 52° C. and the results are shown in FIG. 9. FIG. 9 shows Trypan blue exclusion versus exposure time of cells placed in a water bath of 42° C., 47° C. and 52° C.

As shown in FIG. 9, cells exposed to temperatures of 42° C. experience negligible cell death, even after up to 105 minutes. Cells exposed to temperatures of 47° C. begin to die rapidly after 15 minutes, which is almost three times as long as the time to which the cells were exposed for the pulse experiments. Cells exposed to 52° C. show a 10% decrease in viability after 2 minutes. In the pulse experiments, the longest period of time that the cells encountered the highest temperature used, 47° C., was less than 10 minutes (one minute to heat the sample plus slightly more than 8 minutes to be exposed to 4,500 pulses at a repetition rate of 9 pps at 52 kV/cm).

Trypan Blue Exclusion Four Hours After Exposure to Pulsed Electric Fields

In order to determine the effects of temperature in conjunction with pulsing, experiments were performed where 1,000 and 2,000 200-ps long pulses were applied to the sample at various temperatures (FIG. 9). The temperatures of the sample during pulsing and without pulsing (sham) were 25° C., 37° C., 42° C. and 47° C. Two types of controls were taken: An unpulsed sample at room temperature (25° C.) and an unpulsed sample at each elevated temperature. Four hours after experimental conditions were applied, the Trypan blue assay was performed, the uptake of which is a marker for cell death [8]. The measured electric field was kept constant at 84±7 kV/cm (room temperature). However, due to the changes of the load with temperature, the actual electric field strength for higher temperatures was less than 84 kV/cm. For 25° C. the electric field value was 84 kV/cm, 80 kV/cm for 37° C., 79 kV/cm for 42° C. and 78 kV/cm for 47° C. The specific energy for 1,000 and 2,000 pulses (at room temperature) was 19 J/cm$^3$ and 39 J/cm$^3$, respectively. The specific energy increases with temperature as a result of an increase in conductivity of the medium. At 47° C., the specific energy is increased from 19 and 39 J/cm$^3$ to 25 and 49 J/cm$^3$ for 1,000 and 2,000 pulses, respectively.

Figure 10A:
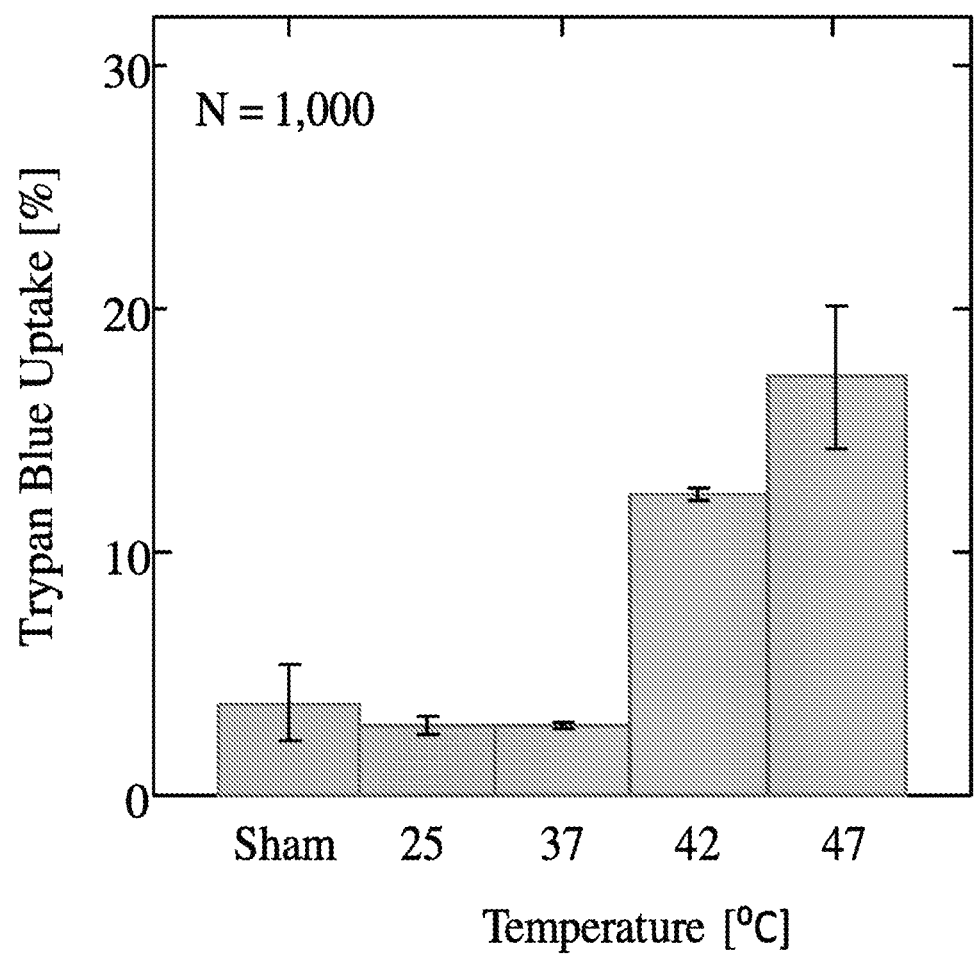
FIGS. 10A and 10B show Trypan blue uptake 4 hours after experimental exposure to 1000 and 2000 pulses of 200 ps, respectively, dependent on temperature.
Figure 10B:
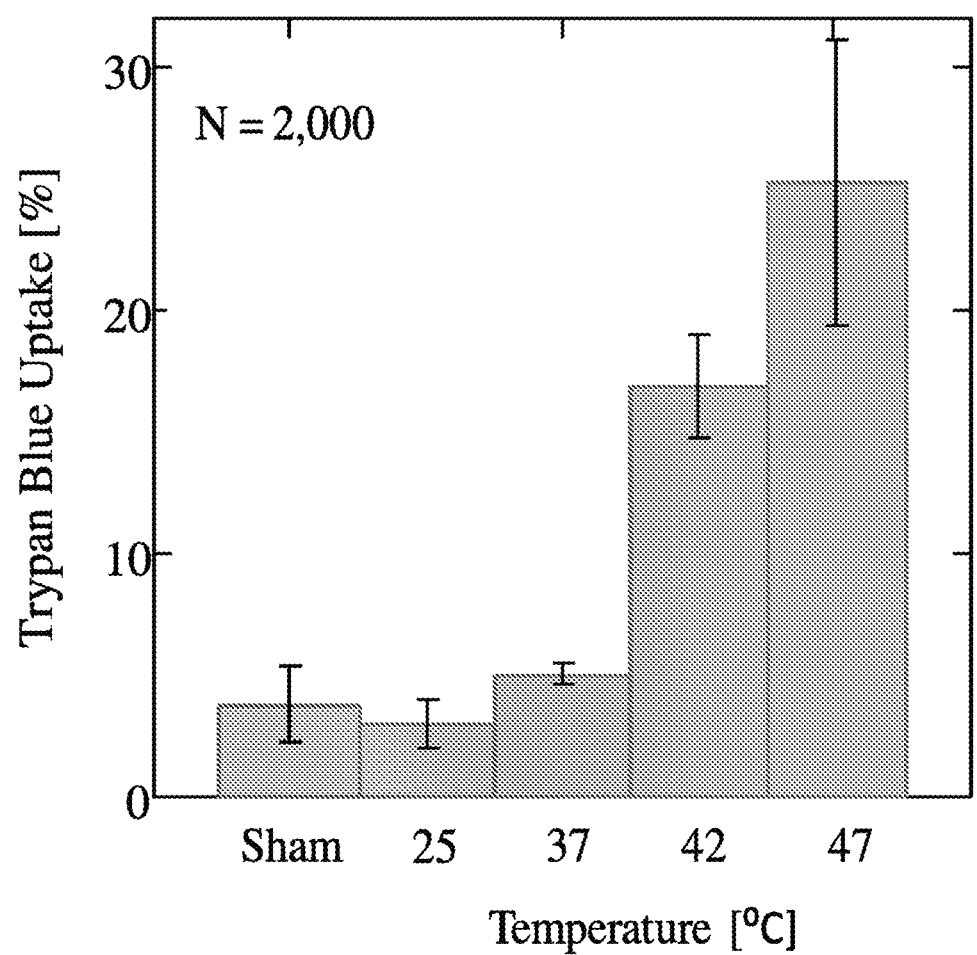

The sham, shown in FIGS. 10A and 10B, is the combination of all the controls performed through the experiment.

In each case, there was no distinguishable difference in the amount of Trypan blue uptake for cells exposed to temperatures up to 47° C. without applying pulsed electric fields for exposure times of less than 10 minutes, as shown in FIG. 9. This time is still long compared to the time it took to apply the largest number of pulses, 2000, at the lowest repetition rate (7 pps).

For both 1,000 and 2,000 pulses, there is a negligible difference in the amount of Trypan blue uptake from the sham and cells exposed to 25° C. and 37° C. during pulsing, as shown in FIGS. 10A and 10B. FIGS. 10A and 10B show Trypan blue uptake 4 hours after experimental exposure to 1000 and 2000 pulses of 200 ps, respectively, dependent on temperature. The measured electric field was kept constant at 84 kV/cm at room temperature. The data are based on 3 to 5 experiments each (n=3-5).

As shown in FIG. 10A, the cell concentration which shows Trypan blue uptake increases to 12.4% and 17.2% when the temperature of the sample is increased to 42° C. and 47° C., respectively. The same trend is seen when 2,000 pulses are applied, as in FIG. 10B, but to a higher degree (17% for 42° C. and 25% for 47° C.).

Cell Death: Immediate Membrane Permeabilization or Apoptosis

In order to determine whether or not the cells were permeabilized by the electric fields or if the cell death is a result of a delayed biological process (apoptosis), Trypan blue was added to the sample prior to pulsing in a separate set of experiments. One minute after exposure, the cells were examined for membrane integrity. This was done for the following conditions;
  (a) 47° C., 78 kV/cm, N=2000, 1000, 100
  (b) 47° C., 61 kV/cm, N=3306.
  (c) 25° C., 84 kV/cm, N=2000

Condition (b) is such that the electrical specific electrical energy is equivalent to condition (a) for an N of 2,000. The results are compared to the 4 hour results in Table 2.

TABLE 2

Trypan blue uptake of cells immediately after pulsing and four hours later (Avg.; average value, Std: standard deviation) Temperature = 47° C.

| | | 78 kV/cm | | 61 kV/cm |
|---|---|---|---|---|
| Time Point | Sham | N = 1,000 | N = 2,000 | N = 3306 |
| 0 hr (Avg.) | 0.9% | 16% | 24% | 3% |
| 0 hr (Std.) | 0.7% | 2.4% | 4% | 2% |
| 4 hr (Avg.) | 3.8% | 17% | 25% | 6% |
| 4 hr (Std.) | 1.6% | 3% | 6% | 0.6% |

As can be seen from Table 2, there was no difference between the sham at 47° C. and results of measurements at 25° C. (not shown). The measurements at 62 kV/cm and at 80 kV/cm were conducted at the same specific electrical energy. There is a slight increase in cell death for the sham, from less than 1% when probed immediately after pulsing to approximately 3% when measured 4 hours after pulsing. This is a result of the cells being incubated for 4 hours in microfuge tubes. However, this increase is negligible when compared to the cell death caused by the pulsed electric fields at 78 kV/cm. For exposure of the cells to these electric fields it is obvious that cell death occurs immediately after the experimental procedure, likely due to membrane permeabilization.

Cell death via secondary processes (apoptosis) seems to be unlikely, since the entire process from the initial trigger to the destruction of cells, can take hours or even days. But events beginning with the first mitochondrial changes and leading to activation of caspases often take about ten minutes. However, it is the time from stimulus to the point of no return referred to above that is rate-limiting in apoptosis. Given results using nsPEFs in Jurkat cells and E4 squamous carcinoma cells in vitro, cytochrome c release and caspase activation events occur within 0.5 to 3 hours. Therefore, it is reasoned that apoptosis markers were not likely to occur within 6 minutes. However, since these results were obtained with nanosecond pulses and the pulses used in this study are in the picosecond range, apoptosis could occur more rapidly in these studies.

There is no statistical difference in the amount of Trypan blue uptake for the sham and for the case that the electric field is reduced to 61 kV/cm (condition b), although the specific electrical energy has not been reduced. This indicates that the electric field needs to exceed a threshold value for the membrane permeabilization.

Electric Field Threshold

Figure 11:
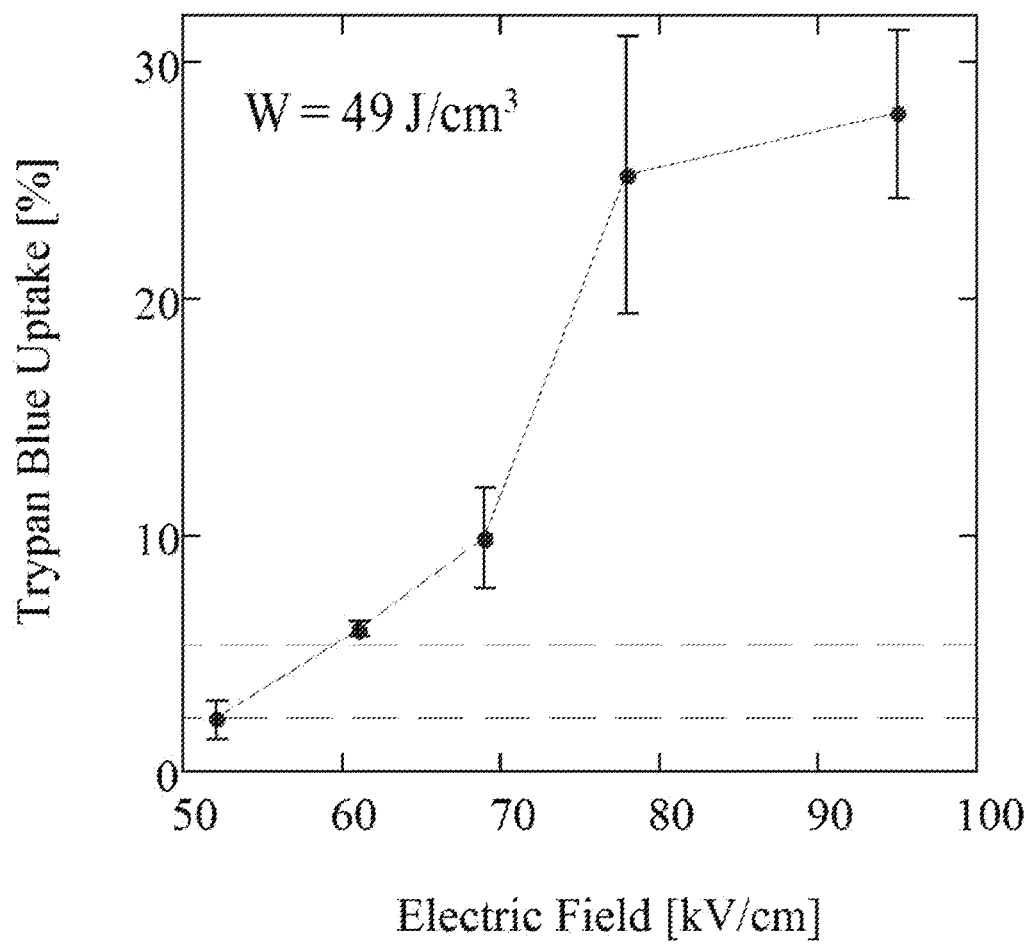
FIG. 11 shows Trypan blue uptake 4 hours after experimental exposure at 47° C.

The dependence of Trypan blue uptake (cell death) on the electric field intensity has been explored by varying the electric field between 52 kV/cm and 95 kV/cm, keeping the specific electrical energy constant at 49 J/cm$^3$. The study was performed for a temperature of 47° C., where the strongest effect on the cells was observed. The results, with n=3, are shown in FIG. 11. FIG. 11 shows Trypan blue uptake 4 hours after experimental exposure at 47° C. The specific electrical energy, W, was kept constant by decreasing the pulse number for an increase in electric field strength. The dashed lines show the range of the sham results.

The results were taken 4 hours after exposure to the 200 ps pulses. At 52 kV/cm, there is no indication of Trypan blue uptake, or cell death, respectively, beyond that observed in the sham studies. The sham control (average±standard deviation) is represented by the dashed gray lines. The concentration cells which show Trypan blue uptake increases strongly above 70 kV/cm, but seem to level off for electric field values exceeding 80 kV/cm. Obviously there is a minimum electric field which needs to be applied to cause considerable membrane permeabilization, independent of the specific electrical energy.

Temperature Effect on the Electrical Properties of the Cell

The measured conductivity and permittivity of the cytoplasm and plasma membrane derived by TDR analysis, with respect to temperature are shown in Table 3. It is worth noting that the buffer (medium) used in dielectric spectroscopy to determine the electrical properties of the cell has a much lower conductivity than the cell culture medium.

TABLE 3

Permittivity and conductivity of cytoplasm and plasma membranes of Hepa 1-6 cells at 25° C., 37° C., 42° C. and 47° C.

| | Relative Permittivity | | | |
|---|---|---|---|---|
| | Membrane | | Cytoplasm | |
| Temperature | Avg. | Std. | Avg. | Std. |
| 25° C. | 13.9 | 0.19 | 76.3 | 2.6 |
| 37° C. | 15.1 | 0.31 | 100 | 1.5 |
| 42° C. | 16.5 | 0.64 | 115 | 4.9 |
| 47° C. | 18 | 0.17 | 146 | 4.8 |

| | Conductivity | | | |
|---|---|---|---|---|
| | Membrane [$10^{-5}$ S/m] | | Cytoplasm [$10^{-1}$ S/m] | |
| Temperature | Avg. | Std. | Avg. | Std. |
| 25° C. | 2.44 | 0.28 | 3.79 | 0.08 |
| 37° C. | 4.05 | 0.13 | 4.53 | 0.07 |
| 42° C. | 5.13 | 0.24 | 4.73 | 0.27 |
| 47° C. | 9.21 | 0.21 | 5.1 | 0.23 |

The change in conductivity of the cytoplasm for the same temperature rise is 34%. However, the temperature effect on the plasma membrane conductivity is much more pronounced: it increases by 270% when the temperature is increased from 25° C. to 47° C. The permittivity of the cytoplasm and plasma membrane of Hepa 1-6 cells increases by approximately 90%, and 30%, when the temperature is raised from 25° C. to 47° C., respectively The increase in permittivity has consequences for the membrane voltage, for the case that electrical pulses are applied with pulse durations less than the dielectric relaxation time of the cytoplasm, as will be shown in the discussion.

Discussion

The effect of cell death is clearly dependent on the temperature at which the cells are pulsed, as shown in FIGS. 10A-10C. It also depends on whether or not the electric field reaches a critical value as shown in FIG. 11. This value depends on the voltage across the membrane, in that a critical voltage is needed for the onset of electropermeabilization or electroporation. The fact that the uptake of Trypan blue immediately follows pulsing indicates that membrane permeabilization is caused by the electric field acting directly on the plasma membrane, rather than due to secondary effects such as those caused by apoptosis 25.

The voltage induced across the membrane at the poles of the cell, $V_m$, relative to the applied voltage across the sample, $V_o$, can be expressed as $$\frac{V_m}{V_o} = \frac{Z_m}{Z_m + Z_c + Z_{med}} \quad (5)$$

where $Z_m$, $Z_c$, and $Z_{med}$ is the impedance of the membrane, cytoplasm and medium, respectively. For pulse durations small compared to the dielectric relaxation time, the impedance can be replaced by the reactance, such that the impedance is determined by the dielectric properties of the material. The dielectric relaxation time is $$\tau_r = \varepsilon/\sigma \quad (6)$$

where ε and σ are the permittivity and conductivity, respectively. For the plasma membrane, this value, using the data in Table 3, is always very large compared to the pulse duration (µs range). For the cytoplasm, again according to the results shown in Table 3, the relaxation time ranges from 1.8 ns (at 25° C.) to 2.5 ns (at 47° C.), and is consequently still large compared to the pulse duration of 200 ps. However, the relaxation time of the medium, using the values listed in Table 1, decreases from 500 ps to 280 ps when the temperature is increased from 25° C. to 47° C., times which are on the order of the pulse duration. In the three-layer model (medium, membrane and cytoplasm) the cytoplasm and membrane can be considered as dielectrics only, whereas the medium must be treated as a lossy dielectric, with a non-negligible conductivity. The voltage across the membrane at the peak of a pulse with triangular shape can, in this case, be expressed as [9]:

$$V_m(\tau) = E_{med} \cdot \frac{d_m}{2 \cdot \varepsilon_m} \cdot (\tau_r \cdot \sigma_{med} + 2 \cdot \varepsilon_{med}) \quad (7)$$

$$V_m(\tau) = E_{med} \cdot \frac{d_m}{2 \cdot \varepsilon_m} \cdot (\tau_r \cdot \sigma_{med} + 2 \cdot \varepsilon_{med})$$

in which $\tau_r$ is the risetime of the pulse, which for a triangular pulse is the same as the pulse duration, τ, at FWHM, $d_m$ is the thickness of the membrane, $\sigma_{med}$ is the conductivity of the medium, and $\varepsilon_m$ and $\varepsilon_{med}$ are the permittivity of the membrane and medium, respectively. For a low cell concentration ($6 \cdot 10^6$ cells/mL in our case), the voltage across the cells alone can be neglected compared to the total voltage applied across the suspension. Therefore $E_{med}$ can be considered the applied electric field, $E_o$.

With an electric field of 84 kV/cm, a membrane thickness of 7 nm, and permittivity and conductivity values taken from Tables 1 and 3, the applied voltage across the membrane is 400 mV, 343 mV, 298 mV and 265 mV for temperatures of 25° C., 37° C., 42° C., and 47° C., respectively. The calculated membrane voltages indicate that an increase in temperature results in a decrease in the membrane voltage. Thus, temperature can shift the electroporation threshold, as illustrated in FIG. 12.

Figure 12:
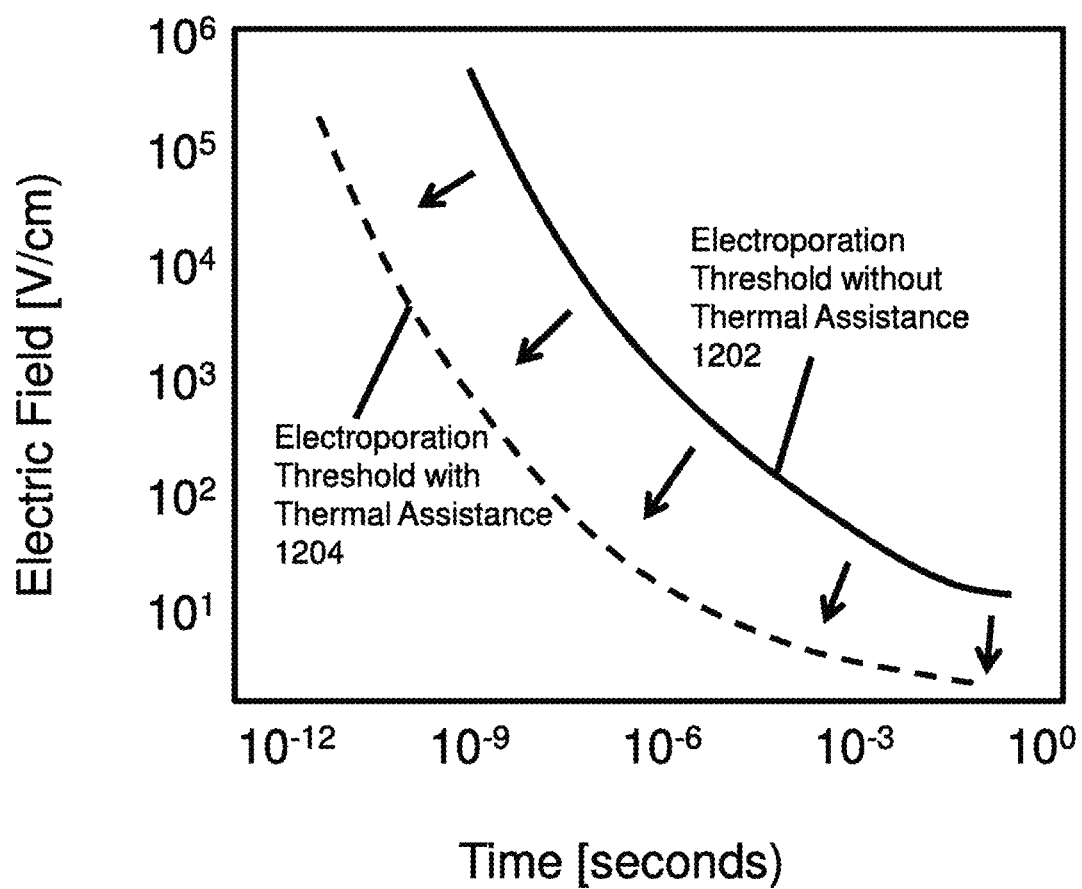
FIG. 12 shows schematically the range of electroporation for mammalian cells in an electric field versus pulse duration (time) diagram.

FIG. 12 shows schematically the range of electroporation for mammalian cells in an electric field versus pulse duration (time) diagram. It is the range above the solid curve (1202) which holds if the temperature is at or below the physiological temperature. The values of electric field intensity and pulse duration are estimates. Pulse number, pulse repetition rate, pulse shape and of course the target, tissue and type cells are parameters which affect the threshold for electroporation. But the solid curve (1202) shows clearly, that for short pulses the required electric field is higher than for long pulses. The reduction in electric field intensity when increasing the pulse duration from ps to ms can span four to five orders of magnitude.

FIG. 12 also shows the effect of increasing temperature on the electroporation threshold, as indicated schematically by the arrows and the dashed curve (1204). The magnitude of the shift in the electroporation curve is dependent the temperature. For higher temperatures above the physiological temperature, the shift becomes larger, as indicated by the results of the 200 ps study where the Trypan blue uptake, a measure considered to be related to the electroporation of the cells, increased with increased temperature, or the electric field could be reduced in order to achieve the same result at elevated temperatures. Important is for controlled electroporation that the temperature must be elevated only for a time which is less than the time for hyperthermia, a purely thermal effect.

The threshold voltage for electroporation across a mammalian cell varies, but is generally assumed to be 1 V. However, measurements of the membrane voltage at room temperature when 60 ns long pulses were applied to Jurkat cells showed that the position of the cell with respect to the direction of the electric field played a role in determining the threshold value for electropermeabilization or electroporation. Voltages of up to 1.6 V could be reached at the anodic pole on a time scale of less than the temporal resolution of the measurements (5 ns) before the membrane voltage leveled off. The membrane voltage at the cathodic pole increased slower, over a time of 15 ns to only 0.6 V, a value which indicates the threshold for electropermeabilization at this pole.

The calculated membrane voltages are even less than the required electropermeabilization voltage for the cathodic pole. In addition, since the pulses in this study are applied for less than 200 ps, a much shorter duration than in the experiments described in reference [30], even if the membrane voltages would reach and exceed 0.6V, it would be unlikely, at temperatures below the physiological temperature, that pore formation can be achieved within this time frame. This is because, as reported from molecular dynamics simulations, it takes a few hundred picoseconds for the electric fields to re-orient the polar lipid head groups and the water to intrude into the membrane molecular structure. This is an important initiating step in the formation of localized water nanowires, followed by pore development. Only the effect of multiple pulses, according to our measurements, enables the permeabilization of the plasma membrane and consequently the influx of Trypan blue.

Figure 13:
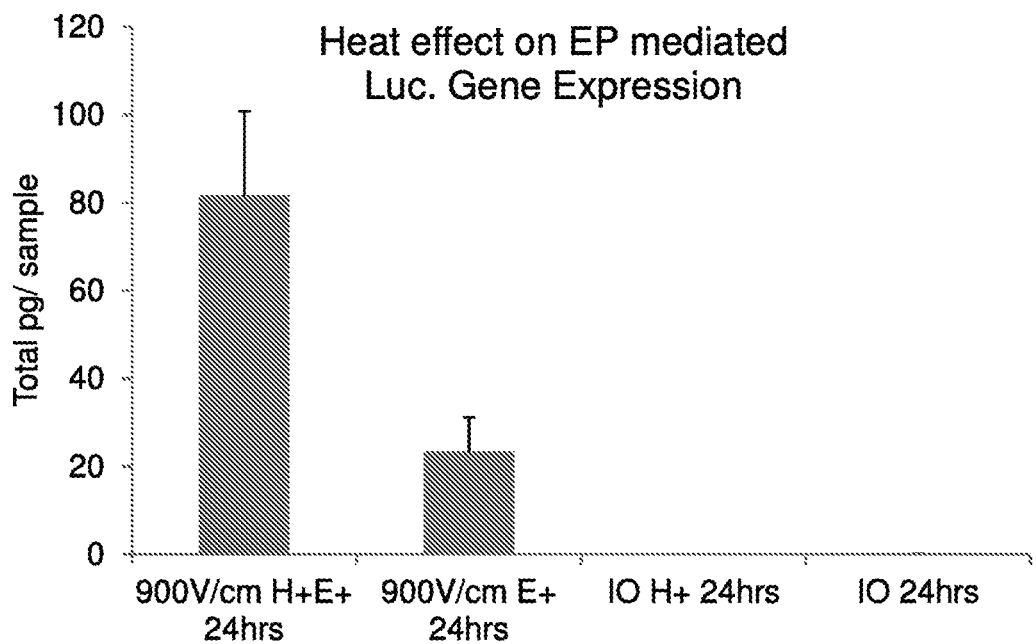
FIG. 13 is a plot of expression levels following delivery of a plasmid encoding luciferase with or without electroporation and with or without heat.
Figure 14:
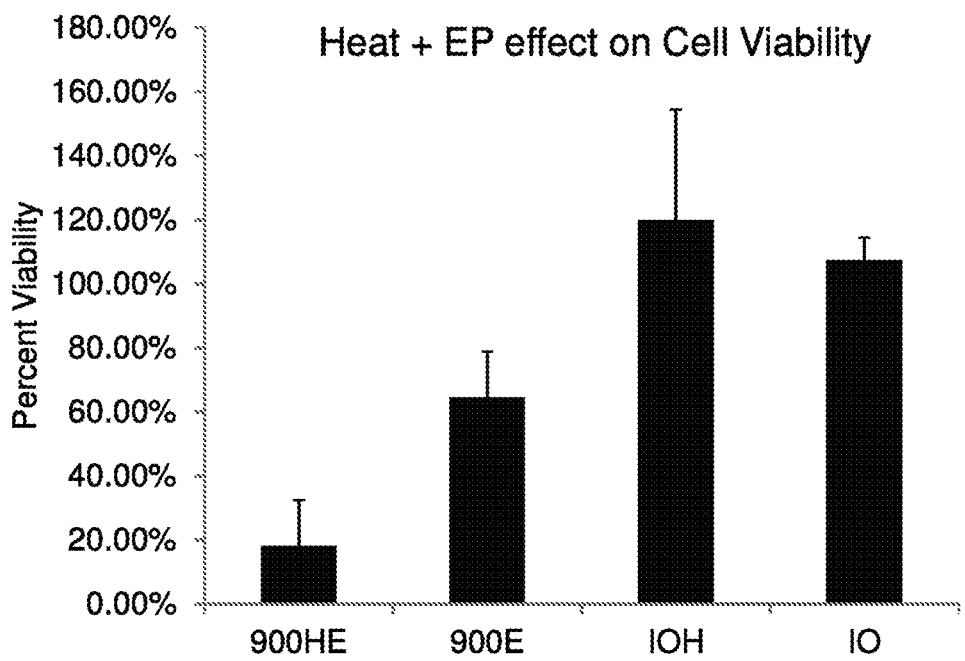
FIG. 14 shows viability of cells that were treated as described above with respect to FIG. 13.

Additionally, the influx of other types of agents is enabled by the permeabilization, as shown in FIGS. 13 and 14. FIG. 13 is a plot of expression levels following delivery of a plasmid encoding luciferase with or without electroporation and with or without heat. In FIG. 13, H=heat; E=electroporation and IO=injection only. For these experiments, human keratinocyte cells were placed in a cuvette and exposed to specific conditions. Cells were at a concentration of 5,000,000 cells/ml and 140 microliters were placed in the cuvette (70,000 cells). Cells that were exposed to heat were brought to a temperature of 43 C. For the H+E+, cells were exposed to electroporation pulses of 900 V/cm 5 ms duration and 1 pulse while being maintained at 43 C. Cells that were only electroporated (E+) received the same electroporation condition but at ambient temperature. For IO cells, they were mixed in the cuvette with the plasmid and the temperature raised to 43° C. The results clearly indicate that when heat is combined with electroporation a significant increase in expression can be obtained. In this example, the same electroporation conditions were utilized. One could extrapolate that if a lower field strength was used with heat you could obtain the same expression as with the electroporation without the heat. So, this demonstrates that one can increase the level of expression by adding heat and also suggests that with heat one can get similar expression with a lower applied voltage.

FIG. 14 shows viability of cells that were treated as described above with respect to FIG. 13. The results show that the heat+electroporation group had higher expression but also lower viability. This illustrates that not only does this combination increase delivery but also increases the killing effects of the electric pulses. As discussed above with respect to FIG. 13, one could lower the applied voltage with heat and as stated above obtain similar expression levels, but also similar or better viability.

Figure 15:
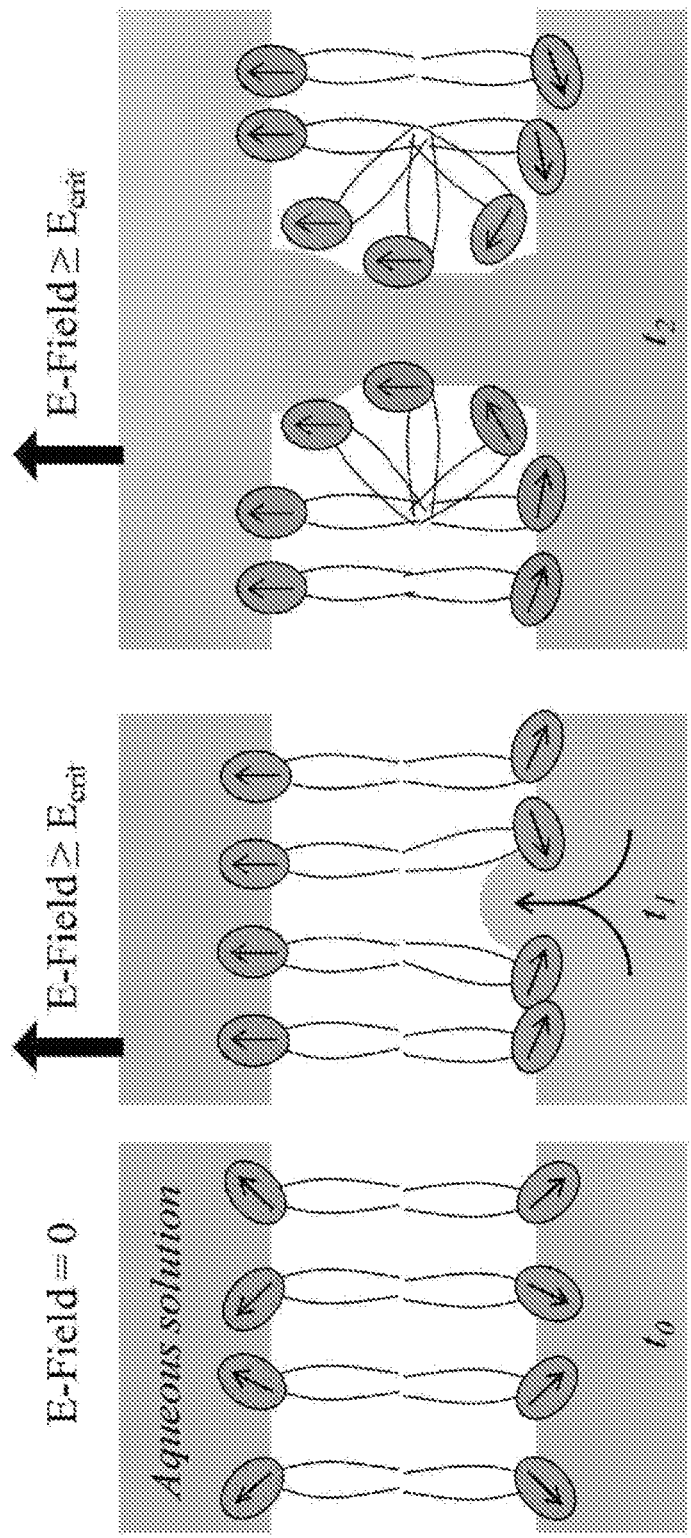
FIG. 15 shows the evolution of a pore formation due to an external electric field.

Another aspect that must be taken into consideration for membrane permeabilization with short pulses is the temperature effect on the membrane viscosity or fluidity, and pore formation enthalpy. The formation of a pore in a lipid bilayer plasma membrane in depicted in FIG. 15. FIG. 15 shows the evolution of a pore formation due to an external electric field. At $t_0$, the heads of the lipids are in random motion. At $t_1$, an external electric field is applied and the lipid heads facing the cathode will align with the electric field. The heads of the lipids facing the anode will rotate to try and align, causing repulsion between them. This repulsion may cause an opening to allow the aqueous solution through the membrane as depicted at time $t_2$.

The dipole heads of the lipids are in random thermal motion when no electric field is applied. The positive charge is towards the aqueous solution, leaving the negative charge toward the interior of the membrane. With the application of an external electric field, the dipoles facing the cathode will align with the electric field and the bonds may lengthen somewhat. However, the force on the lipids facing the anode will cause the polar heads to swing around as shown in FIG. 15 for time $t_1$. This will cause the positive side of the polar heads to repel one another leaving space for the aqueous solution to enter the membrane as depicted with the dark blue arrows. Thus water intrusion into the lipid structure can commence, and would be the start of a poration process. Eventually, a water-wire (or bridge) through the lipid bilayer would form. The intrusion of water molecules would simultaneously push the hydrophobic leaflets causing them to rotate as depicted in FIG. 15 at time $t_2$. These water intrusions are expected to initiate at random sites based on instantaneous local potentials, and zig-zag along into the lipid bilayer, much like "lightening streamers". This can lead to the formation of a pore. This process depends on the viscosity and thermal motion of the membrane, in that a less viscous membrane requires less energy to create a pore.

This observation is evident in the molecular dynamic simulations of a lipid layer with constant electric field strength of 0.5 V/nm at 25° C. and 47° C. The high background electric field is typically used in molecular dynamics simulations to probe poration. It serves as an accelerated test of the pore formation process, since low electric fields would take inordinately long simulation time. The simulation results of FIG. 16 are in agreement with the experimental trends in that no pore formation occurs at 25° C. FIG. 16 shows molecular dynamic simulations of a lipid bilayer exposed to a constant electric field strength of 0.5 V/nm for 1 ns at 0.5 ns, 0.75 ns and 1 ns for 25° C. and 47° C. However, at 47° C., there is a clear indication of pore formation at 0.75 ns which increases at 1 ns. The MD results, by showing snapshots of membrane poration at two specific temperatures, point to the possibility that relatively modest variations in temperature can result in different degrees of electrically stimulated bio-effects. The results underscore the role of temperature in facilitating and accelerating the poration process.

The effect of the decrease in viscosity with temperature, which is believed to be the main cause of the lowering of the threshold for electroporation, overcomes the computed decrease in membrane voltage with temperature. This leads to a considerable reduction of the specific electrical energy required to achieve cell death, compared to pulsed electric field effects at (or less than) physiological temperature. This is obvious when the required specific energies for Trypan blue uptake after 800 ps pulse exposure, in experiments where the temperature was kept below the physiological temperature, are compared with those used in this study. Although different cell types were used—melanoma cells in the 800 ps pulse studies compared to Hepa 1-6 cells in this study, the strong reduction in the specific energy is obvious. In the 800 ps studies at temperatures below 37° C. the specific energy required to achieve a 25% reduction in viability was 2 kJ/cm$^3$. It was reduced to 49 J/cm$^3$ for the 200 ps pulses at elevated temperatures of 47° C., a reduction by a factor of forty. Although it is known that Hepa cells require less energy to induce cell death compared to melanoma cells, by increasing the temperature above the physiological value, the reduction in the specific energy, or the gain in efficiency, likely exceeds one order of magnitude.

This is all the more surprising since a scaling law for membrane permeabilization predicts that, for shorter pulses, a higher specific energy is required to obtain identical results. This scaling law, which provides a scaling or similarity parameter, S, is based on the assumption that the intensity of an observed bioelectric effect depends on the amount of electrical charges passing through the membrane when a pulse is applied. The effect of pulse number, N, is determined by a statistical (thermal) motion of the cells between pulses:

$$S = S(E \cdot \tau \cdot \sqrt{N}) \tag{8}$$

where E is the electric field intensity and $\tau$ the pulse duration. Bursts of pulses with the product of these three quantities being the same should produce identical results. According to this scaling law, pulses shorter by about a factor of 4, as is the case for 800 and 200 ps pulses, would require a four times higher electric field, or a four times higher specific energy (which scales with $E^2\tau$). In our results, we observe the opposite: the specific energy, required for a given uptake of Trypan blue decreases by a factor 40 when we reduce the pulse duration from 800 ps to 200 ps. This counterintuitive effect could be due in part to the differences in cells used in the two studies, but more likely it is caused by the differences in temperature in the two experiments.

In summary, Trypan blue uptake by liver cancer cells, indicating cell death, was found to increase strongly with increasing temperature above the physiological temperature, when bursts of 200 ps pulses were applied to cells in vitro. With 2,000 pulses at 78 kV/cm and a temperature of the biological sample of 47° C., approximately 25% of the cells took up Trypan blue. Experiments at this elevated temperature without pulsing showed that the cells can survive at these temperatures for about 15 minutes before any fatalities were experienced. Since this is long compared to the time the cells were kept at this temperature under pulsed conditions (<6 minutes), cell death due solely to elevated temperatures can be excluded. The observed cell death can therefore not be attributed to temperature alone, but must be a synergistic effect of temperature and pulsed electric fields.

The peak electric field intensity of the subnanosecond pulses needed to exceed 70 kV/cm to enable Trypan blue uptake. Increasing the electric fields beyond this value caused a steep increase in the numbers of cells dying, but seems to level off at electric fields exceeding 80 kV/cm. The specific electrical energy in this study was kept below 60 J/cm$^3$. This is more than an order of magnitude less than recorded for experiments on B16 cells with 800 ps pulses. The cause of cell death was due to instant (relative to the time it took to measure the effect after pulsing) membrane permeabilization, rather than apoptosis, demonstrated through experiments where Trypan blue was added to the suspension before pulsing. The increased sensitivity of cells to pulsed electric fields with temperature is assumed to be due to reduced viscosity of the plasma membrane at elevated temperatures. Water intrusions into the membrane are expected to be initiated at random sites based on the instantaneous local potentials, leading to pore formation. This process depends on the viscosity and thermal motion of the membrane, in that a less viscous membrane requires less energy to create a pore at higher temperatures. Molecular dynamics simulations have demonstrated the increased probability of pore formation at elevated temperatures.

As noted above, the effects of electromanipulation and cell death are clearly dependent on the temperature at which the cells are pulsed, as shown in FIGS. 10A-10C. It also depends on whether or not the electric field reaches a critical value as shown in FIG. 11. This value depends on the voltage across the membrane, in that a critical voltage is needed for the onset of electropermeabilization or electroporation. The fact that the uptake of Trypan blue immediately follows pulsing indicates that membrane permeabilization is caused by the electric field acting directly on the plasma membrane, rather than due to secondary effects such as those caused by apoptosis.

Generally, in studies of the bioelectric effects of nanosecond and subnanosecond pulses, thermal effects are not considered. This is certainly true for single pulse experiments or multiple pulse experiments with a small number of pulses at a low repetition rate. However, applications of such effects for medical treatments based on tissue ablation, such as skin cancer treatments, require multiple pulses applied at a high repetition rate. The effect of temperature increase for such high repetition rate pulse sequences should not be neglected. Rather than having a negative effect on the medical treatment, short term temperature increases of several degrees Celsius above the physiological temperature, generated either by the pulses themselves or produced through external, local heating, may allow a considerable reduction in the pulse number and amplitude for these treatments.

Further, temporary heating of the cells to temperatures less than ten degrees above the physiological temperature has been found to not cause cell death (for exposures of ten minutes and less). However, this temporary increase in temperature allows a reduction the specific energy of the electrical pulses required for inducing cell death or permeabilization by orders of magnitude compared to using the pulses at physiological temperature and below. The molecular dynamics calculations indicate an increased probability for pore formation in the plasma membrane at increasing temperatures.

It should be noted that for the synergistic effect to occur, it does not matter if the increase in thermal energy is caused by the electrical pulses themselves or through other means of heating, for example through irradiation with lasers or microwave sources. The bioelectric effect on cells at elevated temperatures is also, in our opinion, not restricted to the use of subnanosecond pulses, but likely is relevant for the entire pulse range used for therapeutic applications of electroporation. This synergistic effect of pulsed electric fields and increased, transient temperature opens the possibility to lower the energy of the electrical pulses and pulse sequences, and to better utilize bioelectric effects for therapeutic applications.

Such therapeutic applications could include treatment of tumors in internal organs. One possibility to reach internal organs is the use of antennas. Such treatments would require the application of subnanosecond pulses, as used in this study, in order to obtain a reasonably small focal volume.

However, electrical pulses of any duration can be used in treating tumors of internal organs if surgery is involved in the treatment. This has been successfully demonstrated in in vivo studies with irreversible electroporation, an electrotherapy which utilizes electrodes to deliver the pulses to the tissue. Minimally invasive procedures with catheter electrodes and laparoscopic procedures could be a next step. Local heating of electrically treated tumors, e.g., through pulsed non-ionizing radiation, would then be only a small addition to the electrical procedure performed at the liver or other organs, but with likely benefits.

It should be noted that the combination of thermal and electrical energy is not restricted to treatment of cancer tissue. This therapeutic approach could be utilized to remove or ablate any unwanted tissue. In addition, this approach could be used to manipulate cells and tissues for many therapeutic applications. This can be accomplished by delivering specific therapeutic agents to cells within a target tissue to achieve a desired therapeutic effect.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

REFERENCES

The following references, the contents of which are herein incorporated by reference, each describe various supporting concepts and results.

1. R. Nuccitelli, U. Pliquett, X. Chen, W. Ford, J. Swanson, S. J. Beebe, J. F. Kolb, and K. H. Schoenbach, "Nanosecond pulsed electric fields cause melanomas to self-destruct," Biochem. Biophys. Res. Commun., vol. 343, no. 2, pp. 351-360, 2006.

2. K. H. Schoenbach, B. Hargrave, R. P. Joshi, J. F. Kolb, C. Osgood, R. Nuccitelli, A. Pakhomov, R. J. Swanson, M. Stacey, J. A. White, S. Xiao, J. Zhang, S. J. Beebe, P. F. Blackmore, and E. S. Buescher, "Bioelectric effects of intense nanosecond pulses," IEEE Trans. Dielectr. Electr. Insul., vol. 14, no. 5, pp. 1088-1119, 2007.

3. X. Chen, J. F. Kolb, R. J. Swanson, K. H. Schoenbach and S. J. Beebe, "Apoptosis initiation and angiogenesis inhibition: Melanoma targets for nanosecond pulsed electric fields," Pigment Cell and Melanoma Research, vol. 23, pp. 554-563,1 2010.

4. S. Xiao, K. H. Schoenbach, and C. E. Baum, "Time-Domain Focusing Radar for Medical Imaging," Proc. URSI, XXIX Gen. Assembly of URSI, Chicago, Ill., 2008, http://ursi-france.institut-telecom.fr/pages/pages_ursi/URSIGA08/papers/E02p4.pdf.

5. C. E. Baum, "Focal Waveform of a Prolate-Spheroidal IRA", SSN Note, 509, February, 2006.

6. S. Altunc, C. E. Baum, C. Christodoulou, E. Schamiloglu, and C. J. Buchenauer, Focal waveforms for various source waveforms driving a prolate-spheroidal impulse radiating antenna (IRA)," Radio Science, vol. 43, RS4S13 (9 pp), 2008.

7. J. F. Kolb, S. Xiao, J. T. Camp, M. Migliaccio, C. Bajracharya, and K. H. Schoenbach, "Sub-nanosecond electrical pulses for medical therapies and imaging," 2010 Proceedings of the Fourth European Conference on Antennas and Propagation (EuCAP), pp. 1-5, 12-16 April 2010.

8. K. H. Schoenbach, S. Xiao, R. P. Joshi, J. T. Camp, T. Heeren, J. F. Kolb, S. J. Beebe, "The Effect of Intense Subnanosecond Electrical Pulses on Biological Cells," IEEE Trans. Plasma Science , vol. 36, no. 2, pp. 414-422, 2008.

9. J. Thomas Camp, "The Synergistic Effect of Temperature and Subnanosecond Pulsed Electric Fields on Biological Cells," Dissertation, Old Dominion University, May 2012.

10. S. Xiao, S. Guo, V. V. Nesin, R. Heller, and K. H. Schoenbach, "Subnanosecond electric pulses cause membrane permeabilization and cell death," IEEE Trans. Biomed. Eng., vol. 58, no. 5, pp. 1239-1245, 2011.

11. S. Jayaram, G. S. P. Castle, and A. Margaritis, "Effects of High Electric Field Pulses on *Lactobacillus Brevis* at Elevated Temperatures," Conference Record of the 1991 IEEE Industry Applications Society Annual Meeting, vol. 1, pp. 674-681, October 1991.

12. T. Ohshima, K. Okuyama, M. Sato, "Effect of culture temperature on high voltage pulse sterilization of *Escherichia coli*," Journal of Electrostatics, vol. 55, pp. 227-235, 2002.

13. T. Heeren, J. T. Camp, J. F. Kolb, K. H. Schoenbach, S. Katsuki, and H. Akiyama, "250 kV Subnanosecond Pulse Generator with Adjustable Pulsewidth," IEEE Trans. Diel. Electr. Insul., vol. 14, pp. 884-888, 2007.

14. Carl Baum, University of New Mexico, private communication, 2009.

15. ATK Missions System. Tactical Propulsion & Controls Division, 8560 Cinderbed Road, Suite 700. Newington, Va. 2212.

16. L. Sevgi and C. Uluisik, "Transmission Line Fault Analysis Using a Matlab Based Virtual Time Domain Reflectometer Tool," IEEE Ant. and Prop. Mag., pp. 141-145, 2006.

17. A. Garner, G. Chen, N. Chen, V. Sridhara, J. Kolb, R. Swanson, S. Beebe, R. Joshi, and K. Schoenbach, "Ultrashort electric pulse induced changes in cellular dielectric properties", Biochem. Biophys. Res. Comm., vol. 362, pp. 139-144, 2007.

18. J. Zhuang, W. Ren, Y. Jing, J. F. Kolb, "Dielectric Evolution of Mammalian Cell Membranes after Exposure to Pulsed Electric Fields," IEEE Trans. Dielectr. Electr. Insul., vol 19, no. 2, pp. 609-622, 2012.

19. H. J. C. Berendsen, D. van der Spoel D, R. van Drumen, "Gromacs: a message-passing parallel molecular dynamics implementation," Comput. Phys. Commun. vol. 91, pp. 43-56, 1995.

20. E. Lindahl, B. Hess, D. van der Spoel, "A package for molecular simulation and trajectory analysis," J. Mol. Model. vol. 7, pp. 306-317, 2001.

21. D. R. Green, "Apoptotic Pathways: Ten Minutes to Dead," Cell, vol. 121, no. 5, pp. 671-674, 2005.

22. S. J. Beebe, P. M. Fox, L. J. Rec, E. L. Willis, K. H. Schoenbach, "Nanosecond, high-intensity pulsed electric fields induce apoptosis in human cells," FASEB J, vol. 17, no. 11, pp. 1493-1495, t 2003.

23. W. Ren, S. J. Beebe, "An apoptosis targeted stimulus with nanosecond pulsed electric fields (nsPEFs) in E4 squamous cell carcinoma," Apoptosis, vol. 16, pp. 382-393, 2011.

24. K. H. Schoenbach, B. Hargrave, R. P. Joshi, J. F. Kolb, C. Osgood, R. Nuccitelli, A. Pakhomov, J. Swanson, M. Stacey, J. A. White, S. Xiao, J. Zhang, S. J. Beebe, P. F. Blackmore, E. S. Buescher, "Bioelectric Effects of Nanosecond Pulses," IEEE Trans. Diel. Electr. Insul., vol. 14, no. 5, pp. 1088-1109, 2007.

25. G. Kroemer, L. Galluzzi, P. Vandenabeele, J. Abrams, E. S. Alnemri, E. H. Baehrecke, M. V. Blagosklonny, W. S. El-Deiry, P. Golstein, D. R. Green, M. Hengartner, R. A. Knight, S. Kumar, S. A. Lipton, W. Malorni, G. Nunez, M. E. Peter, J. Tschopp, J. Yuan, M. Piacentini, B. Zhivotovsky, G. Melino; Nomenclature Committee on Cell Death 2009. Classification of cell death: Recommendations of the Nomenclature Committee on Cell Death 2009. Cell Death Differ. vol. 16, no. 1, pp. 3-11, 2009.

26. R. P. Joshi, Q. Hu, R. Aly, K. H. Schoenbach, and H. P. Hjalmarson, "Self-Consistent Simulations of Electroporation Dynamics in Biological Cells Sujected to Ultrashort Electrical Pulses," Phys. Rev. E, vol. 64, 011913 pp. 1-10, 2001.

27. J. Gehl, "Electroporation: Theory, and methods, perspectives for drug delivery, gene therapy and research," Acta. Physiol. Scand., vol. 177, pp. 437-447, 2003.

28. J. C. Weaver, "Electroporation of Cells and Tissue," IEEE Trans. Plasma Sci, vol. 28, no. 1, pp. 24-33, 2000.

29. T. Y. Tsong, "Electroporation of Cell Membranes: Minireview," Biophys. J., vol. 60, pp. 297-306, 1991.

30. W. Frey, J. A. White, R. O. Price, P. F. Blackmore, R. P. Joshi, R. Nuccitelli, S. J. Beebe, K. H. Schoenbach, and J. F. Kolb, "Plasma Membrane Voltage Changes During Nanosecond Pulsed Electric Field Exposure," Biophys. J. vol. 90, pp. 3608-3615, 2006.

31. Q. Hu, R. P. Joshi, and K. H. Schoenbach, "Simulations of nanopore formation and phosphatidylserine externalization in lipid membranes subjected to a high-intensity, ultrashort electric pulse," Phys. Rev., vol. 72, pp. 1539-3755, 2005.

32. A. Martiniere, M. Shedunova, A. J. W. Thomson, N. H. Evans, S. Penfieldd, J. Runions, and H. G. McWatters, "Homeostasis of Plasma Membrane Viscosity in Fluctuating Temperatures," New Phytologist, vol. 192, pp. 328-2337, 2011.

33. D. A. Bates, C. L. Grimellec, and J. H. T. Bates, "Effects of Thermal Adaptation at 40° C. on Membrane Viscosity and the Sodium-Potassium Pump in Chinese Hamster Ovary Cells," Cancer Research, pp. 4895-4899, 1985.

34. A. Blicher, K. Wodzinska, M. Fidorra, M. Wnter Halter, and T. Heimburg, "The temperature dependence of lipid membrane permeability, its quantized nature, and the influence of anesthetics," Biophys. J., vol. 96, pp. 4581-4591, June 2009.

35. Q. Hu, V. Sridhara, R. P. Joshi, J. F. Kolb, and K. H. Schoenbach, "Molecular Dynamics Analysis of High Electric Pulse Effects on Bilayer Membranes Containing DPPC and DPPS," IEEE Trans. Plasma Science., vol. 34, no. 4, pp. 1405-1411, 2006.

36. J. Song, R. P. Joshi and K. H. Schoenbach, "Synergistic effects of local temperature enhancements on cellular responses in the context of high-intensity, ultrashort electric pulses," Med. Biol. Eng. Comput., vol. 49, pp. 713-718, 2011.

37. K. H. Schoenbach, R. P. Joshi, S. Beebe, and C. Baum, "A scaling law for membrane permeabilization with nanopulses," IEEE Trans Diel. Electr. Insul., vol.16, no.5, pp.1224-1235, 2009.

38. R. L. Nuccitelli, U. Pliquett, X. Chen, W. Ford, R. J. Swanson, S. J. Beebe, J. F. Kolb, and K. H. Schoenbach, "Nanosecond Pulsed electric fields cause melanomas to self-destruct". Biochem. Biophys. Res. Commun., vol. 343, pp. 351-360, 2006.

39. E. B. Garon, D. Sawcer, P. T Vernier, T. Tang, Y. Sun, L. Marcu, M. A. Gundersen, and H. P. Koeffler, "In vitro and in vivo evaluation and a case report of intense nanosecond pulsed electric field as a local therapy for human malignancies," Intern. J. Cancer, vol. 121, pp. 675-682, 2007.

40. R. Nuccitelli, X. Chen, A. G. Pakhomov, W. H. Baldwin, S. Sheikh, J. L. Pomicter, W. Ren, C. Osgood, J. F. Kolb, S. J. Beebe, and K. H. Schoenbach, "A New Pulsed Electric Field Therapy for Melanoma Disrupts the Tumor's Blood Supply and Causes Complete Remission without Recurrence," Intern. J. Cancer, vol. 125, pp. 438-445, 2009.

41. K. R. Thomson, W. Cheung, S. J. Ellis, D. Federman, H. Kavnoudias, D. Loader-Oliver, S. Roberts, P. Evans, C. Ball, and A. Haydon, "Investigation of the safety of irreversible electroporation in humans," J Vasc. Interv. Radiol. Vol. 22, pp. 611-21, 2011.

42. C. R. Schmidt, P. Shires and M. Mootoo, "Real-time ultrasound imaging of irreversible electroporation in a porcine liver model adequately characterizes the zone of cellular necrosis," HPB (Oxford), vol. 14, pp. 98-102, 2012.

What is claimed is:

1. A method for treatment of biological tissues comprising a target tissue, comprising:
    causing a temperature of the target tissue to be elevated and maintained at a treatment temperature range which is above a physiological temperature of the biological tissues and at or below about 47° C.;
    generating, during the causing, an electric field extending through at least a portion of the target tissue using a pre-defined sequence of short duration voltage pulses applied between at least two electrodes; and
    synchronizing maintaining of the treatment temperature range to overlap with applying the pre-defined sequence of short duration voltage pulses, and wherein the pre-defined sequence of short duration voltage pulses is selected such that a magnitude of the electric field is configured to deliver an electrical energy sufficient to induce cell death in the portion of the target tissue at the treatment temperature range and that is lower than a specific electrical energy sufficient to induce cell death in the portion of the target tissue at or below the physiological temperature.

2. The method of claim 1, wherein the treatment temperature range is between about 40° C. and about 47° C.

3. The method of claim 1, wherein the treatment temperature range is maintained at least throughout a time period while the sequence of short duration voltage pulses is applied.

4. The method of claim 1, where the generating comprises selecting a duration of the short duration voltage pulses to be between about 50 ps and about 800 ms.

5. The method of claim 1, wherein the generating comprises selecting the pre-defined sequence of short duration voltage pulses so that a magnitude of the electric field is between about 20 V/cm and about 1000 kV/cm.

6. The method of claim 1, wherein the method is combined with an introduction of pharmacological or biological agents to the target tissue.

7. The method of claim 1, wherein the target tissue is a tumor tissue or adipose tissue.

8. The method of claim 1, wherein a source of the temperature elevation comprises at least one of a lamp, a laser, a light emitting diode, a microwave source, or a millimeter wave source operating with a wavelength in the range between about 0.4 micrometers and about 10 cm.

9. The method of claim 1, the method comprising elevating the temperature of the target tissue via at least one of a lens, a mirror or reflector, an optical fiber, or a waveguide coupled to a source of the temperature elevation.

10. The method of claim 1, wherein the elevating further comprises:
    inserting one of a needle or a catheter into the biological tissue; and
    activating a source of temperature elevation.

11. A control unit configured to couple to a pulse generator, the control unit configured for: causing the pulse generator to generate a pre-defined sequence of short duration voltage pulses for delivery to a target tissue resulting in an electric field, wherein a temperature of the target tissue has been elevated and maintained at a treatment temperature range above a physiological temperature of biological tissues and at or below about 47° C., and synchronizing maintaining of the treatment temperature range to overlap with causing the pre-defined sequence of short duration voltage pulses, wherein the pre-defined sequence of short duration voltage pulses is configured to cause a magnitude of the electric field to deliver an electrical energy sufficient to induce electromanipulation in a portion of the target tissue at the treatment temperature range, and wherein the delivered electrical energy is lower than a specific electrical energy sufficient to induce electromanipulation in the portion of the target tissue at or below the physiological temperature.

12. The control unit of claim 11, wherein inducing electromanipulation comprises inducing cell death.

13. The control unit of claim 11, wherein the pulse generator is caused to provide a duration of the short voltage pulses to be between about 50 ps and about 800 ms.

14. The control unit of claim 11, wherein the control unit comprises one or more control units and wherein one of the one or more control units is coupled to a source of temperature elevation, the control unit is further configured to control and synchronize operation of the pulse generator and the source of the temperature elevation.

15. The control unit of claim 11, wherein the control unit comprises at least two separate control units, the first control unit configured to control operation of a source of temperature elevation in response to a temperature of the target tissue measured by a temperature probe.

16. The control unit of claim 11, wherein the treatment temperature range is between about 40° C. and about 47° C.

17. The control unit of claim 11, wherein the pre-defined sequence of short voltage pulses is selected such that an electric field is generated that is between 20 V/cm and 1000 kV/cm.

18. A system for treatment of biological tissues comprising a target tissue, comprising:
    a pulse generator configured for generating electromagnetic energy in the form of a plurality of voltage pulses;
    a plurality of electrodes coupled to the pulse generator and arranged so that an electric field resulting from the plurality of pulses and between the plurality of electrodes traverses at least a portion of the target tissue; and
    a processor coupled to the pulse generator, the processor configured for:
        causing the pulse generator to generate a pre-defined sequence of short duration voltage pulses at least during a time period when a temperature of the target tissues is elevated and maintained at a treatment temperature range which is above a physiological temperature of the biological tissue and at or below about 47° C.,
        wherein the pre-defined sequence is configured to cause a magnitude of the electric field to deliver an electrical energy sufficient to induce cell death in the portion of the target tissue at the treatment temperature range, and wherein the delivered electrical energy is lower than a specific electrical energy sufficient to induce cell death in the portion of the target tissue at or below the physiological temperature.

19. The system of claim 18, further comprising a source of temperature elevation wherein the processor or a different processor is coupled to the source of the temperature elevation.

20. The system of claim 19, comprising a control unit configured to control and synchronize operation of the pulse generator and the source of the temperature elevation.

21. The system of claim 18, further comprising a temperature probe for measuring temperature of at least the portion of the target tissue.

22. The system of claim 18, the system includes at least one guide device comprising at least one of a lens, a mirror, an optical fiber, or a waveguide.

23. The system of claim 22, wherein the optical fiber or the waveguide is disposed in at least one of a needle, a catheter, or laparoscopic probe insertable into the biological tissue.

24. The system of claim 18, wherein the plurality of electrodes comprises electrode plates, needle electrodes, or a combination of both.

* * * * *

UNITED STATES PATENT AND TRADEMARK OFFICE
CERTIFICATE OF CORRECTION

PATENT NO. : 10,660,693 B2  
APPLICATION NO. : 16/057115  
DATED : May 26, 2020  
INVENTOR(S) : Karl H. Schoenbach et al.

Page 1 of 1

It is certified that error appears in the above-identified patent and that said Letters Patent is hereby corrected as shown below:

In the Specification

In Column 1, Line 26, before the "FIELD OF THE INVENTION", please insert the following language:
-- STATEMENT REGARDING FEDERALLY SPONSORED RESEARCH OR DEVELOPMENT
This invention was made with government support under NIH EB018956 awarded by The National Institute of Health. The government has certain rights in the invention. --

Signed and Sealed this  
Nineteenth Day of October, 2021

Drew Hirshfeld  
*Performing the Functions and Duties of the*  
*Under Secretary of Commerce for Intellectual Property and*  
*Director of the United States Patent and Trademark Office*